(12) United States Patent
Elliott et al.

(10) Patent No.: US 11,857,792 B2
(45) Date of Patent: Jan. 2, 2024

(54) METHODS FOR STIMULATION OF CRANIAL NERVES

(71) Applicant: NuXcel2, L.L.C., Reno, NV (US)

(72) Inventors: Lynn Elliott, Maple Grove, MN (US); Stephen C. Masson, Jr., Raleigh, NC (US)

(73) Assignee: NuXcel2, L.L.C., Reno, NV (US)

( * ) Notice: Subject to any disclaimer, the term of this patent is extended or adjusted under 35 U.S.C. 154(b) by 0 days.

(21) Appl. No.: 17/860,346

(22) Filed: Jul. 8, 2022

(65) Prior Publication Data

US 2022/0346666 A1    Nov. 3, 2022

Related U.S. Application Data

(63) Continuation of application No. PCT/US2021/012723, filed on Jan. 8, 2021.
(Continued)

(51) Int. Cl.
*A61N 1/36* (2006.01)
*A61N 1/05* (2006.01)
(Continued)

(52) U.S. Cl.
CPC .............. *A61N 1/3611* (2013.01); *A61B 5/08* (2013.01); *A61B 5/11* (2013.01); *A61N 1/0551* (2013.01);
(Continued)

(58) Field of Classification Search
CPC .......... A61N 1/05; A61N 1/0551; A61N 1/36; A61N 1/3611; A61B 5/08; A61B 5/11; A61B 5/4836
See application file for complete search history.

(56) References Cited

U.S. PATENT DOCUMENTS

| 8,116,883 B2 | 2/2012 | Williams et al. |
| 8,574,164 B2 | 11/2013 | Mashiach |
| | (Continued) | |

FOREIGN PATENT DOCUMENTS

| JP | 2010512843 A | 4/2010 |
| JP | 2011500143 A | 1/2011 |
| | (Continued) | |

OTHER PUBLICATIONS

"U.S. Appl. No. 17/858,668, Preliminary Amendment filed Jul. 6, 2022".
(Continued)

*Primary Examiner* — Christopher A Flory
(74) *Attorney, Agent, or Firm* — Schwegman Lundberg & Woessner, P.A.

(57) ABSTRACT

Neuromodulation of cranial nerves can be used to treat sleep or breathing disorders, among other diseases and disorders. A neuromodulation system can include a housing configured for implantation in an anterior cervical region of a patient, such as at or under a mandible of the patient, such as at least partially in one or more of a submental triangle, a submandibular triangle, and a carotid triangle. The system can include an electrode lead coupled to the housing, and the electrode lead can include an electrode configured to be disposed at or near a cranial nerve target in the patient. The system can be configured to generate electrical neuromodulation signals for delivery to the cranial nerve target using the electrode.

22 Claims, 15 Drawing Sheets

Related U.S. Application Data

(60) Provisional application No. 62/959,617, filed on Jan. 10, 2020.

(51) Int. Cl.
*A61B 5/08* (2006.01)
*A61B 5/11* (2006.01)
*A61N 1/375* (2006.01)
*A61B 5/00* (2006.01)

(52) U.S. Cl.
CPC ....... *A61N 1/0556* (2013.01); *A61N 1/36078* (2013.01); *A61N 1/36125* (2013.01); *A61N 1/37518* (2017.08); *A61B 5/4836* (2013.01)

(56) References Cited

U.S. PATENT DOCUMENTS

| | | | |
|---|---|---|---|
| 9,889,299 B2 | 2/2018 | Ni et al. | |
| 2008/0103545 A1* | 5/2008 | Bolea | A61N 1/37229 607/42 |
| 2010/0094379 A1* | 4/2010 | Meadows | A61N 1/37264 607/48 |
| 2010/0241195 A1* | 9/2010 | Meadows | A61N 1/3611 607/2 |
| 2011/0112601 A1* | 5/2011 | Meadows | A61N 1/37223 607/42 |
| 2011/0213438 A1* | 9/2011 | Lima | A61N 1/37223 607/42 |
| 2013/0072747 A1* | 3/2013 | Mashiach | A61N 2/02 607/42 |
| 2013/0085546 A1* | 4/2013 | Bolea | A61N 1/3601 607/42 |
| 2013/0085558 A1 | 4/2013 | Mashiach | |
| 2014/0039579 A1* | 2/2014 | Mashiach | A61N 1/36075 607/61 |
| 2014/0228905 A1 | 8/2014 | Bolea | |
| 2015/0094962 A1* | 4/2015 | Hoegh | G16H 50/30 702/19 |
| 2015/0142120 A1 | 5/2015 | Papay | |
| 2015/0148860 A1* | 5/2015 | Lima | A61N 1/36167 607/42 |
| 2015/0224307 A1* | 8/2015 | Bolea | A61N 1/3611 607/42 |
| 2016/0030740 A1* | 2/2016 | Mashiach | A61N 1/37211 607/42 |
| 2016/0199651 A1* | 7/2016 | Meadows | A61N 1/36185 607/42 |
| 2017/0007829 A1 | 1/2017 | Gross | |
| 2017/0029615 A1 | 2/2017 | He et al. | |
| 2017/0106190 A1 | 4/2017 | Papay | |
| 2018/0013347 A1 | 1/2018 | Paul et al. | |
| 2018/0133474 A1 | 5/2018 | Meadows et al. | |
| 2019/0151604 A1 | 5/2019 | Harper et al. | |
| 2020/0086078 A1 | 3/2020 | Poltorak | |
| 2020/0129762 A1 | 4/2020 | Toong et al. | |
| 2020/0281763 A1 | 9/2020 | Scheiner | |
| 2020/0282219 A1* | 9/2020 | Scheiner | A61N 1/36057 |
| 2022/0339439 A1* | 10/2022 | Ron | A61N 1/0548 |
| 2022/0339441 A1 | 10/2022 | Elliott et al. | |
| 2023/0026728 A1 | 1/2023 | Elliott et al. | |

FOREIGN PATENT DOCUMENTS

| | | |
|---|---|---|
| JP | 2012504467 A | 2/2012 |
| JP | 2019503722 A | 2/2019 |
| JP | 2023510548 A1 | 3/2023 |
| WO | WO-2018132412 A1 | 7/2018 |
| WO | WO-2021142278 A1 | 7/2021 |

OTHER PUBLICATIONS

"International Application Serial No. PCT/US2021/012723, International Search Report dated Mar. 18, 2021", 2 pgs.

"International Application Serial No. PCT/US2021/012723, Written Opinion dated Mar. 18, 2021", 9 pgs.

U.S. Appl. No. 17/790,573, filed Jul. 1, 2022, Systems and Methods for Stimulation of Cranial Nerves.

U.S. Appl. No. 17/858,668, filed Jul. 6, 2022, Multiple-Housing Implantable Systems for Stimulation of Cranial Nerves.

"International Application Serial No. PCT US2021 012723, International Preliminary Report on Patentability dated Jul. 21, 2022", 11 pgs.

"Japanese Application Serial No. 2022-542496, Voluntary Amendment filed Aug. 30, 2022", w English Claims, 11 pgs.

"U.S. Appl. No. 17/790,573, Non Final Office Action dated Jan. 19, 2023", 12 pgs.

"U.S. Appl. No. 17/858,668, Response filed Mar. 13, 2023 to Restriction Requirement dated Jan. 12, 2023", 9 pgs.

"U.S. Appl. No. 17/858,668, Restriction Requirement dated Jan. 12, 2023", 7 pgs.

"U.S. Appl. No. 17/790,573, Advisory Action dated Aug. 11, 2023", 4 pgs.

"U.S. Appl. No. 17/790,573, Final Office Action dated May 9, 2023", 13 pgs.

"U.S. Appl. No. 17/790,573, Response filed Apr. 19, 2023 to Non Final Office Action dated Jan. 19, 2023", 15 pgs.

"U.S. Appl. No. 17/790,573, Response filed Jul. 10, 2023 to Final Office Action dated May 9, 2023", 18 pgs.

"U.S. Appl. No. 17/790,573, Response filed Sep. 11, 2023 to Advisory Action dated Aug. 11, 2023", 20 pgs.

"U.S. Appl. No. 17/858,668, Examiner Interview Summary dated May 22, 2023", 3 pgs.

"U.S. Appl. No. 17/858,668, Final Office Action dated Jul. 19, 2023", 30 pgs.

"U.S. Appl. No. 17/858,668, Non Final Office Action dated Apr. 20, 2023", 23 pgs.

"U.S. Appl. No. 17/858,668, Response filed May 23, 2023 to Non Final Office Action dated Apr. 20, 2023", 15 pgs.

"European Application Serial No. 21738734.9, Response filed Aug. 9, 2023 to Extended European Search Report dated May 15, 2023", 31 pgs.

"Japanese Application Serial No. 2022-542496, Notification of Reasons for Rejection dated Sep. 5, 2023", W/English Translation, 10 pgs.

"European Application Serial No. 21738734.9, Extended European Search Report dated May 15, 2023", 8 pgs.

"U.S. Appl. No. 17/790,573, Final Office Action dated Sep. 28, 2023", 9 pgs.

"U.S. Appl. No. 17/790,573, Notice of Allowance dated Sep. 28, 2023", 9 pgs.

"U.S. Appl. No. 17/858,668, Response filed Oct. 19, 2023 to Final Office Action dated Jul. 19, 2023", 15 pgs.

* cited by examiner

METHODS FOR STIMULATION OF CRANIAL NERVES

CROSS-REFERENCE TO RELATED APPLICATIONS

This patent application is a continuation of International Application No. PCT/US2021/012723, filed Jan. 8, 2021, and published as WO 2021/142278 on Jul. 15, 2021, which claims the benefit of priority to U.S. Provisional Patent Application No. 62/959,617, filed on Jan. 10, 2020, which are incorporated by reference herein in their entirety.

BACKGROUND

Neural function can impact various disorders such as including cardiovascular disorders, movement disorders and tremors, epilepsy, depression, respiratory disorders (e.g., chronic obstructive pulmonary disease (COPD), pleural effusion), sleep disorders (e.g., obstructive sleep apnea (OSA)), obesity, xerostomia, and facial pain disorders. These disorders impact millions of patients and impact their quality of life and longevity. Obstructive sleep apnea, for example, is a common sleep disorder. Individuals suffering from OSA experience interrupted breathing patterns during sleep. Chronic, severe sleep apnea can require treatment to prevent sleep deprivation and other sleep-related complications. Obstructive sleep apnea is prevalent in patients with cardiovascular disease, is a cause of hypertension, and is associated with increased incidence of stroke, heart failure, atrial fibrillation, and coronary heart disease. Severe OSA is associated with an increase in all-cause and cardiovascular mortality.

In an example, external or implanted muscle stimulation devices or neurostimulation devices can be provided to excite tissue structures in or near an airway, such as to help treat sleep apnea or to counter apneic and hypopneic events.

In an example, neurostimulation can be used to treat a variety of disorders other than OSA. For example, neurostimulation can be used to treat epilepsy, depression, heart failure, obesity, pain, migraine headaches, COPD, or other disorders.

BRIEF SUMMARY

Neuromodulation of cranial nerves can be used to treat various diseases and disorders, including sleep disorders or breathing disorders. A neuromodulation system can include a housing configured for implantation in an anterior cervical region of a patient, such as at or under a mandible of the patient, such as at least partially in one or more of a submental triangle, a submandibular triangle, and a carotid triangle. The system can include an electrode lead coupled to the housing, and the electrode lead can include an electrode configured to be disposed at or near a cranial nerve target in the patient. The system can be configured to generate electrical neuromodulation signals for delivery to the cranial nerve target using the electrode. In an example, the cranial nerve target can include one or more of a hypoglossal nerve, a glossopharyngeal nerve, a trigeminal nerve, a facial nerve, or a vagus nerve, among others.

Implantable systems for delivery or titration of neuromodulation therapy can optionally include multiple housings, such as can be implanted in different portions of an anterior cervical region of a patient. For example, a first housing including electrostimulation circuitry can be implanted in a submental triangle, a submandibular triangle, or a carotid triangle of the anterior cervical region. A second housing, such as including a battery or other circuitry, can be implanted in a different one of the submental triangle, the submandibular triangle, or the carotid triangle. Implanting different portions of a system in different cervical locations can situate circuitry proximate various neural targets, and can help maintain patient comfort, among other benefits.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
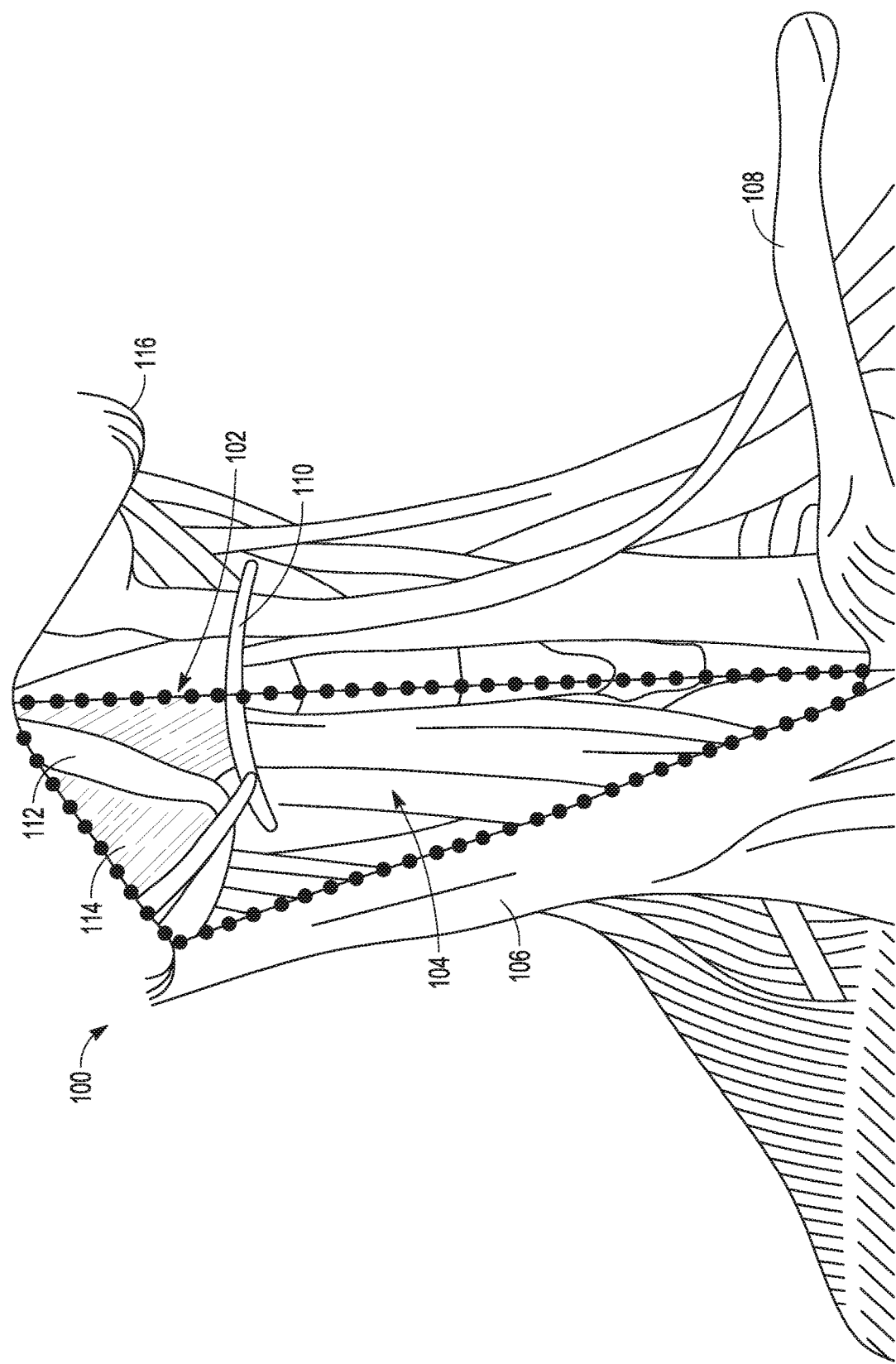
FIG. 1 illustrates generally a first anatomic example of front view of an anterior cervical region of a human.

Systems, devices, and methods discussed herein can be configured for electrical stimulation of cranial nerves. Examples discussed herein can include methods for implanting a neuromodulation system or methods for using an implanted system to deliver neuromodulation therapy to one or more target cranial nerves, or to sense physiologic information about a patient, such as to monitor a disease state or control a neuromodulation therapy or other therapy. In an example, system or device features discussed herein can facilitate implantation of devices, leads, sensors, electrostimulation hardware, or other therapeutic means on or near cranial nerve tissue. In an example, the present subject matter includes systems and methods for implanting a neuromodulation device near or below an inferior border of a mandible (i.e., the body or ramus of the mandible or jaw bone) in an anterior triangle of the neck (e.g., located in the medial aspect), or in a posterior triangle of the neck (e.g., located in the lateral aspect), or in multiple regions of the neck.

The present inventors have recognized that a problem to be solved can include providing a minimally invasive neuromodulation therapy or treatment system that can provide signals to neural targets in or near a cervical region of a patient. The problem can include treating, among other things, obstructive sleep apnea (OSA), heart failure, hypertension, epilepsy, depression, post-traumatic stress disorder (PTSD), attention deficit hyperactivity disorder (ADHD), craniofacial pain syndrome, facial palsy, migraine headaches, xerostomia, atrial fibrillation, stroke, autism, inflammatory bowel disease, chronic inflammation, chronic pain, tinnitus, rheumatoid arthritis, or fibromyalgia. The problem can include providing an implantable system that is resistant to migration or dislocation when the system is installed in a motion-prone body region such as in a neck or cervical region of a patient. The problem can further include stimulating multiple different cranial nerve targets concurrently or in a coordinated manner to provide an effective therapy.

The present inventors have recognized, among other things, that a solution to the above-described problems can include a neuromodulation system that can be implanted in an anterior cervical region of a patient, such as at or under a mandible of the patient. In an example, the system can include a housing that can be coupled to tissue in or near an anterior triangle, such as to digastric muscle or tendon tissue, to mylohyoid muscle tissue, to a hyoid bone, or to a mandible, among other locations. The present inventors have recognized that the solution can include a device configured for wireless communication with an external power source or programmer, for example, with a communication device implanted at or near the housing in the anterior cervical region of the patient. The present inventors have recognized that the solution can include an implantable device with multiple electrode leads, such as can extend from a housing in multiple different directions, to interface with multiple different cranial nerves. The present inventors have recognized that the solution can further include or use physiologic information, such as can be sensed from a patient using implanted or external sensors or patient inputs, to update one or more characteristics of a therapy provided to the patient by the neuromodulation system.

The present inventors have recognized that the neuromodulation systems and methods discussed herein can be used to treat OSA, among other disorders or diseases. In an example, an OSA treatment can use a neuromodulation device that is implanted in one or more of a submental triangle and a submandibular triangle, and an electrode lead with electrodes that are configured to be disposed at or near one or more targets on a hypoglossal nerve, vagus nerve, glossopharyngeal nerve, or trigeminal nerve (e.g., at a mandibular branch of the trigeminal nerve). In an example, the solution can include using multiple electrodes or electrode leads to deliver a coordinated, bilateral stimulation therapy to cranial nerve targets, such as to anterior and posterior branches of the hypoglossal nerve. The therapy can be configured to selectively stimulate or block a neural pathway that influences activity of one or more of tongue muscles, mylohyoid muscles, stylohyoid muscles, digastric muscles, or stylopharyngeus muscles of a patient, to thereby treat OSA.

The description that follows describes systems, methods, techniques, instruction sequences, and computing machine program products that illustrate example embodiments of the present subject matter. In the following description, for purposes of explanation, numerous specific examples and aspects are set forth in order to provide an understanding of various embodiments of the present subject matter. It will be evident, however, to those skilled in the art, that embodiments of the present subject matter may be practiced in various combinations. Unless explicitly stated otherwise, structures (e.g., structural components, such as modules or functional blocks) are optional and may be combined or subdivided, and operations (e.g., in a procedure, algorithm, treatment, therapy, or other function) can vary in sequence or can be combined or divided.

In an example, the implantable neuromodulation systems and devices discussed herein can comprise a control system, signal or pulse generator, or other therapy signal generator, such as can be disposed in one or more housings that can be communicatively coupled to share power and/or data. The housings can comprise one or more hermetic enclosures to protect the circuitry or other components therein. In an example, a housing can include one or more headers, such as can comprise a rigid or flexible interface for connecting the housing, or circuitry or components inside of the housing, with leads or other devices or components outside of the housing. In an example, a header can be used to couple signal generator circuitry inside the housing with electrodes or sensors outside of the housing. In an example, the header can be used to couple circuitry inside the housing with a telemetry antenna, wireless power communication devices (e.g., coils configured for near-field communications or NFC), or other devices, such as can be disposed on or comprise flexible substrates or flexible circuits. This system configuration allows the housing(s), lead(s), and flexible circuits to be implanted in different anatomic locations, such as in a neck or cervical region of a patient. In an example, the various system components can be implanted in one or more of the anatomic triangular regions or spaces in the cervical region, and leads or other devices external to a circuitry housing can be tunneled to other locations, including at various cranial nerve targets. Accordingly, various therapeutic elements can be implanted on or near target cranial nerves, and sensing elements can be implanted on or near the same or other cranial nerves or at other anatomic structures in the same or different locations. Some components can be located in a different anatomic location, such as in a different cervical region than is occupied by a housing. For example, a telemetry antenna or NFC coil can be provided at or near a surface of the skin, while a housing with circuitry that coordinates neuromodulation therapy or power signal management can be implanted elsewhere, such as more deeply within one of the anterior triangle spaces of the neck.

In an example, multiple different housings can comprise a neuromodulation system, and the different housings can contain different control circuitry, power sources, sensors, or other components. The different housings and components therein can be tethered or connected, such as wirelessly or using leads or other flexible circuitry, such as in a serially-connected, daisy-chain configuration or in a star-like configuration. Such system configurations can facilitate implant of one portion of the system in one cervical region, while targeting therapy to a nerve target or sensing physiologic status information or patient activity level or posture from a different region. In an example, a system that is distributed across multiple different areas can help provide flexibility and strain relief from repetitive motion.

The various housings for a cervically-implanted neuromodulation system can have various sizes, shapes, and features. For example, a housing can include surface contours that can correspond, generally, to contours of a triangular (e.g., in one or more dimensions) cervical region in a patient body. For example, some cervical spaces can include one or more three-dimensional regions or pockets, such as can be represented or defined in part by one or more generally triangular or pyramidal spaces, such as can narrow anteriorly and medially. Accordingly, an implantable device housing can have an oblique or truncated prism shape, such as at or along at least one of its faces, to facilitate positioning in such a pocket or space. In an example, the housing can have a generally cylindrical, prismatic, pyramidal, frustum, or spherical configuration, such as can include prismatic variations with or without parallel sides. For example, a housing configured to be implanted in anterior regions of the neck, such as the submandibular triangle or submental triangle, can have a housing shaped as a rectangular prism with wide sides parallel to a base of the mandible to minimize thickness, lessen patient discomfort, and avoid the submandibular gland. In this example, a lead or leads can extend from a header of the housing to one or more cranial nerves, such as the hypoglossal nerve in the submandibular triangle. Other cranial nerves and implantation sites can similarly be used, such as using similarly or differently shaped housings.

The following discussion introduces various anatomic structures, including various triangle regions in a cervical or neck region. Following introduction of the anatomy, the discussion introduces various devices and features thereof that can be configured to provide neuromodulation to cranial nerve targets, among other targets, such as to treat various disorders, diseases, or symptoms.

FIG. 1 illustrates generally a first anatomic example 100 of a front view of an anterior cervical region of a human. The region generally extends between a clavicle 108 and mandible 116 and can be divided into various additional regions or subregions. In an example, the anterior cervical region includes a pair of anterior triangles on opposite sides of a sagittal midline 102, such as including an anterior triangle 104 as illustrated. The term "midline" as used herein refers to a line or plane of bilateral symmetry in the cervical or neck region of a person. In an example, a midline corresponds to the sagittal plane, that is, is the anteroposterior (AP) plane of the body.

The anterior triangle 104 can include a region that is bounded by the midline 102, a base of the mandible 116, and a sternocleidomastoid muscle, or SCM 106. A hyoid bone 110 can extend between the pair of anterior triangles across the midline 102. The anterior triangle 104 can include, among other things, a digastric muscle 112 (e.g., including anterior and posterior portions of the digastric muscle 112), a mylohyoid muscle 114, and various other muscle, bone, nerve, and other body tissue.

Figure 2:
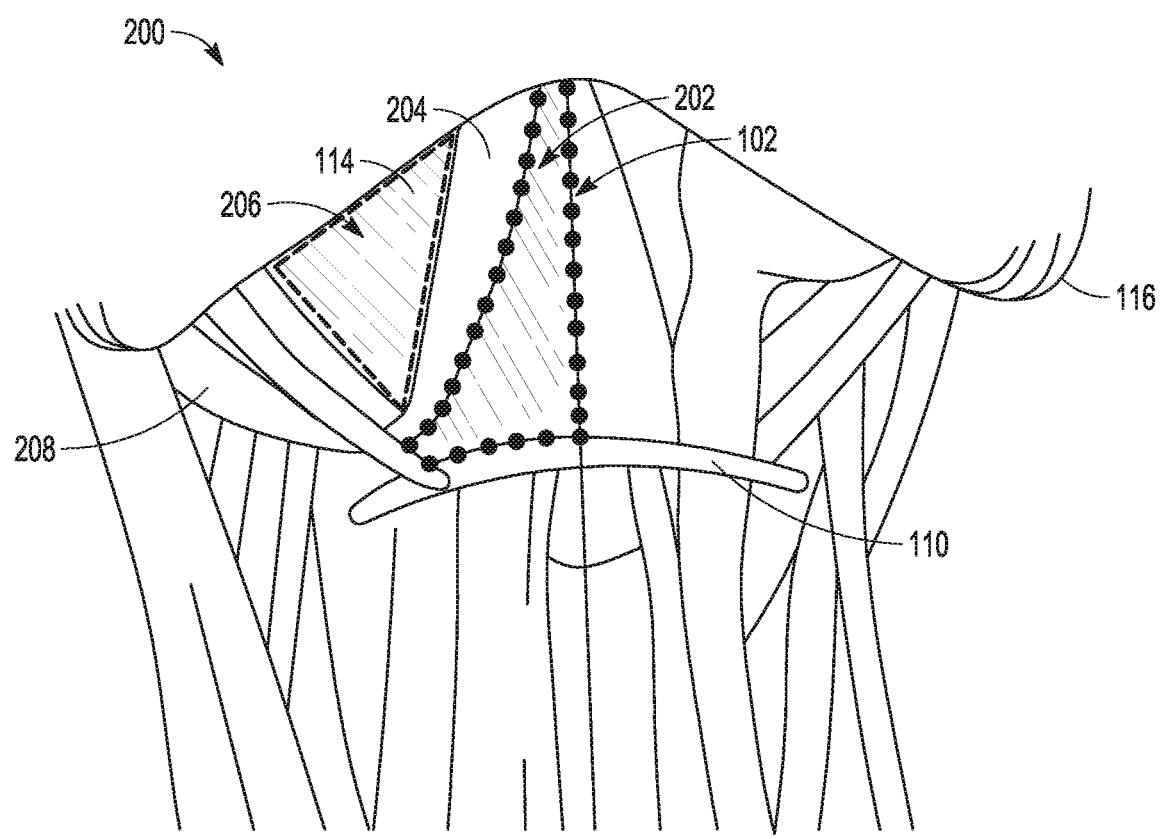
FIG. 2 illustrates generally a second anatomic example that includes a portion of an anterior cervical triangle.

FIG. 2 illustrates generally a second anatomic example 200 that includes a portion of the anterior triangle 104 from the example of FIG. 1. FIG. 2 shows, for example, that the anterior triangle 104 can be divided into various regions, including a submandibular triangle 206, and a submental triangle 202. In an example, the anterior triangle 104 can further include a carotid triangle, as discussed below in the example of FIG. 3. A posterior triangle of the neck (not shown) can be divided into various regions, including an occipital triangle and a supraclavicular triangle.

The submental triangle 202 is generally understood to include a region that is bounded by the midline 102, the hyoid bone 110, and the anterior digastric muscle 204. The submandibular triangle 206 is generally understood to include a region that is bounded by the anterior digastric muscle 204, the posterior digastric muscle 208, and the base of the mandible 116.

Figure 3:
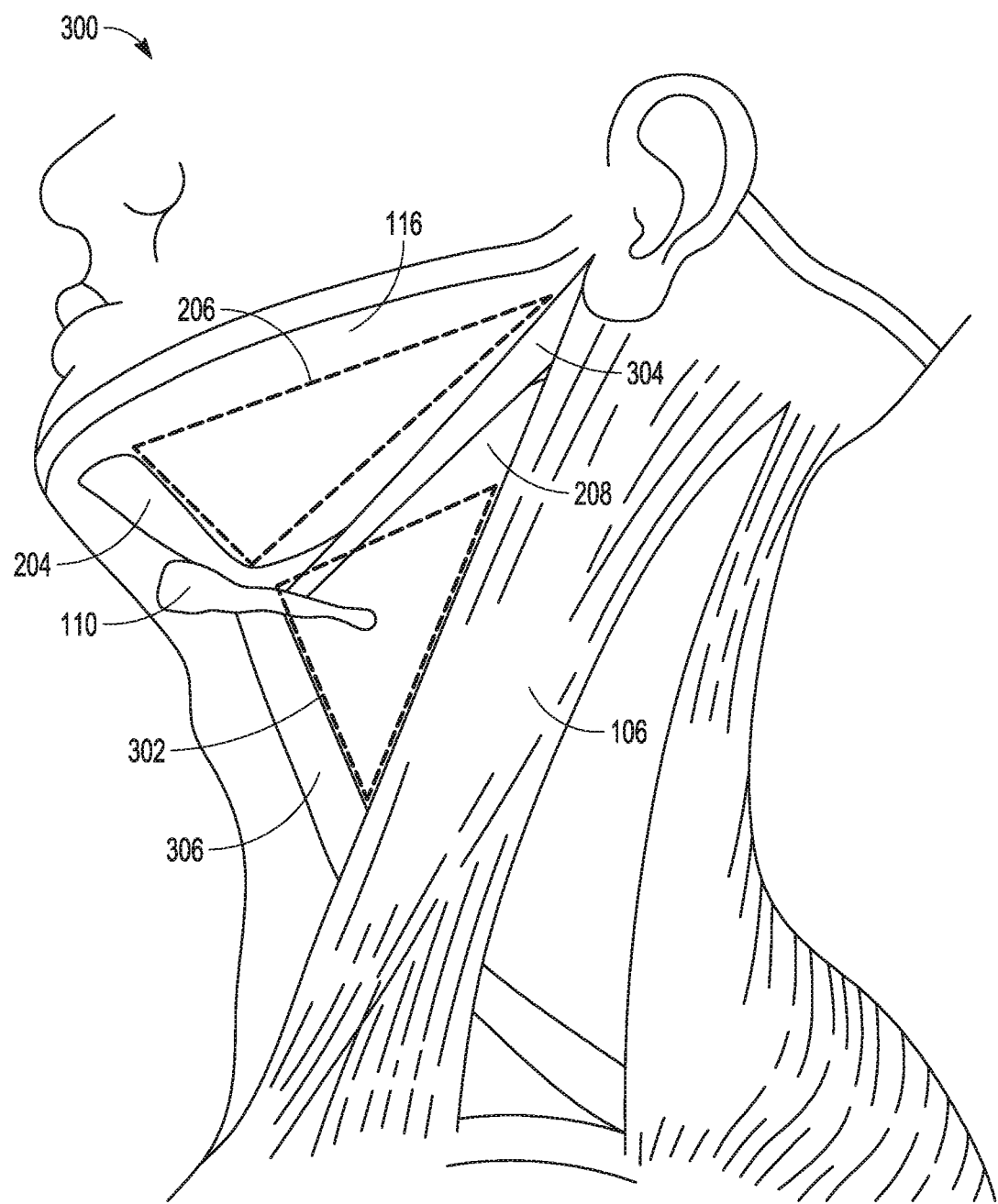
FIG. 3 illustrates generally a third anatomic example that includes a partial side view of an anterior cervical triangle.

FIG. 3 illustrates generally a third anatomic example 300 that includes a partial side view of the anterior triangle 104. The example of FIG. 3 further illustrates the location of the submandibular triangle 206, such as in relation to the anterior digastric muscle 204 and the mandible 116. The example of FIG. 3 illustrates the carotid triangle 302, such as can comprise a portion of the anterior triangle 104 in the cervical region. The carotid triangle 302 is generally understood to include a region that is bounded by the SCM 106, the omohyoid muscle 306, and the posterior digastric muscle 208.

In an example, an implantable neuromodulation device can be implanted in the anterior triangle 104 or in the posterior triangle, such as using the systems and methods discussed herein. In further examples, an implantable neuromodulation device can be implanted in one or more of the submental triangle 202 and the submandibular triangle 206. The implantable neuromodulation device can be configured to provide a stimulation therapy to one or multiple nerve targets such as can be in or near the anterior triangle 104 or the posterior triangle, or to nerve targets that can be accessed via tunneled leads that extend from a housing disposed in the anterior triangle 104 or the posterior triangle. In other words, various regions in the anterior and posterior cervical triangles can provide access to a main body of, or to branches of, various cranial nerves, including the hypoglossal nerve (CN XII), the accessory nerve (CN XI), the vagus nerve (CN X), the glossopharyngeal nerve (CN IX), the facial nerve (CN VII), and the trigeminal nerve (CN V), among others.

The present inventors have realized that the anterior and posterior cervical triangles are anatomic locations suitable for implantation of a neuromodulation system or component thereof. The present inventors have further realized that the locations include various anatomic structures suitable for coupling and therefore stabilizing a neuromodulation system or component thereof. For example, the present inventors have recognized that such coupling structures can include the hyoid bone 110, the connective tissue sling of the hyoid bone 110, the mandible 116, the digastric tendon, the anterior or posterior portion of the digastric muscle 112, the stylohyoid muscle 304, the mylohyoid muscle 114, the omohyoid muscle, or the SCM 106.

Figure 4:
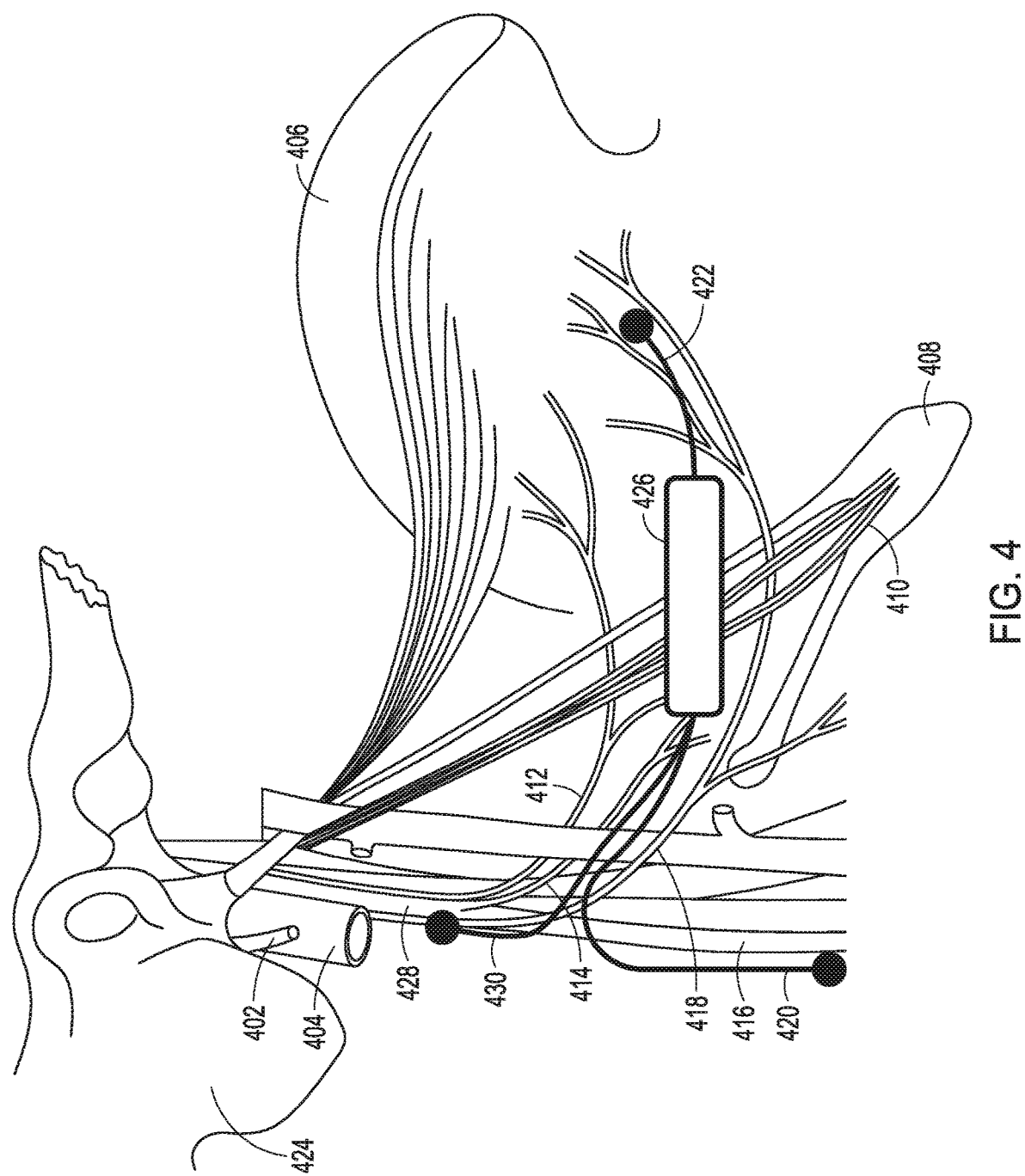
FIG. 4 illustrates generally a fourth anatomic example that includes a partial side view of an anterior cervical triangle.

FIG. 4 illustrates generally a fourth anatomic example 400 that includes a partial side view that includes the anterior triangle 104. The fourth anatomic example 400 illustrates an upper portion of the anterior triangle 104 and a portion of the upper neck, such as at or below a temporal bone 424. A representation of a tongue 406 and of a portion of a jugular vein 404 is included for further context and reference.

The fourth anatomic example 400 shows various nerves and vessels. The illustrated nerves include some, but not all, of the cranial nerves that can be targeted using the neuromodulation systems, devices, and methods discussed herein. For example, nerve targets in the fourth anatomic example 400 include a facial nerve 402, a jugular vein 404, a glossopharyngeal nerve 412, a pharyngeal branch of vagus nerve 414, a vagus nerve 416, a hypoglossal nerve 418, and a mandibular branch of the trigeminal nerve 428, among others.

The example of FIG. 4 includes an example of an implantable therapy device 426. The implantable therapy device 426 can be implanted in a patient in an upper portion of an anterior triangle 104 of a cervical region of the patient. For example, the implantable therapy device 426 can be implanted in one or more of the submental triangle 202 and the submandibular triangle 206. In the example of FIG. 4, the implantable therapy device 426 can be coupled to various anatomical structures, such as a stylohyoid muscle 410, a hyoid bone 408, or other tendons or structures in the upper neck.

The example of FIG. 4 includes multiple leads coupled to the implantable therapy device 426. For example, the implantable therapy device 426 can be coupled to a lower electrode lead 420, an anterior electrode lead 422, and an upper electrode lead 430. The lower electrode lead 420 can be implanted at or near a neural target on the vagus nerve 416, for example, in or adjacent to the carotid triangle 302. In an example, the lower electrode lead 420 can be coupled to the SCM 106 or other structure at or near the vagus nerve 416. The upper electrode lead 430 can be implanted at or near the facial nerve 402, the mandibular branch of the trigeminal nerve 428, or the glossopharyngeal nerve 412, among others. In an example, the anterior electrode lead 422 can be implanted at or near a neural target on the hypoglossal nerve 418. Various details of the implantable therapy device 426 and its associated leads are discussed herein, including in the example of FIG. 5.

In an example, the various implantable devices and components thereof that are discussed herein can be coupled to various anatomic structures or tissues inside a patient body, such to stabilize or maintain a device or component at a particular location and resist device movement or migration as the patient carries out their daily activities. In an example, coupling a device or component to tissue can include anchoring, affixing, attaching, or otherwise securing the device or component to tissue using a coupling feature. A coupling feature can include, but is not limited to, a flap or flange, such as for suturing to tissue (e.g., muscle, tendon, cartilage, bone, or other tissue).

In an example, a coupling feature can include various hardware such as a screw or helical member that can be driven into or attached to tissue or bone. In an example, a coupling feature can include a cuff, sleeve, adhesive, or other component. In an example, one or multiple different coupling features can be used for different portions of the same neuromodulation system. For example, a suture can be used to couple a device housing to a tissue site, and a lead, such as coupled to the housing, can include a distal cuff to secure the lead at or near a neural target.

Figure 5:
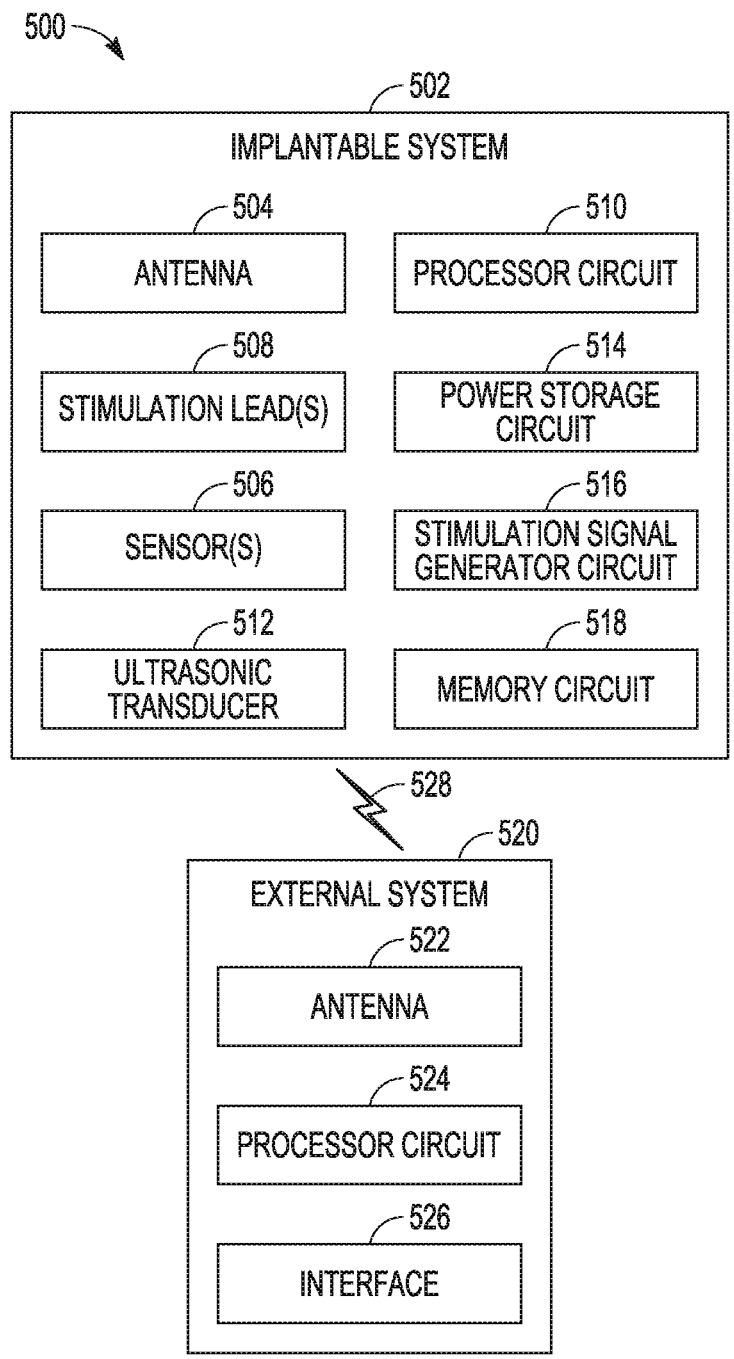
FIG. 5 illustrates generally an example of a system that can be configured to provide a neuromodulation therapy.

FIG. 5 illustrates generally an example of a system 500 that can be configured to provide or control a neuromodulation therapy. The system 500 can include an implantable system 502 and an external system 520. The implantable system 502 and the external system 520 can be communicatively coupled using a wireless coupling 528. In an example, the wireless coupling 528 can enable power signal communication (e.g., unidirectionally from the external system 520 to the implantable system 502), or can enable data signal communication (e.g., bidirectionally between the implantable system 502 and the external system 520). In an example, the implantable system 502 or the external system 520 can be wirelessly coupled for power or data communications with one or more other devices, including other implantable or implanted devices, such as in the same patient body.

In the example of FIG. 5, the implantable system 502 can include an antenna 504, a sensor(s) 506 such as comprising one or more physiologic sensors, a stimulation lead(s) 508, a processor circuit 510, an ultrasonic transducer 512, a power storage circuit 514, a stimulation signal generator circuit 516, and a memory circuit 518, among other components or modules.

In an example, the antenna 504 can include a telemetry antenna such as configured for data communication between the implantable system 502 and the external system 520. In an example, the antenna 504 can include an antenna, such as an NFC coil, that is configured for wireless power communication between the implantable system 502 and the external system 520 or other external power source.

The processor circuit 510 can include a general purpose or purpose-built processor. The memory circuit 518 can include a long-term or short-term memory circuit, such as can include instructions executable by the processor circuit 510 to carry out therapy or physiologic monitoring activities for the system 500. In an example, the processor circuit 510 of the implantable system 502 is configured to manage telemetry or data signal communications with the external system 520, such as using the antenna 504 or other communication circuitry.

In an example, the stimulation signal generator circuit 516 includes an oscillator, pulse generator, or other circuitry configured to generate electrical signals that can provide electrostimulation signals to a patient body, or to power various sensors (e.g., including the sensor(s) 506), or transducers (e.g., including the ultrasonic transducer 512). In an example, the stimulation signal generator circuit 516 can be configured to generate multiple electrical signals to provide multipolar electrostimulation therapy to multiple neural targets, such as concurrently or in a time-multiplexed manner. The stimulation signal generator circuit 516 can be configured to use or provide different neurostimulation signals, such as can have different pulse amplitude, pulse duration, waveform, stimulation frequency, or burst pattern characteristics.

The stimulation signal generator circuit 516 can be used to generate therapy signals for multiple different targets concurrently. For example, signals from the stimulation signal generator circuit 516 can be used to stimulate one cranial nerve target to efferent effect, and to stimulate a different nerve or branch to elicit an afferent response. In another example, one cranial nerve can be blocked while another nerve is stimulated. Other combinations can similarly be used.

In an example, the stimulation lead(s) 508 can include one or more leads that are coupled to or integrated with a housing or header of the implantable system 502. The stimulation lead(s) 508 can be detachable from the housing to facilitate replacement or repair.

In an example, the stimulation lead(s) 508 can include electrostimulation hardware such as electrodes having various configurations, including cuff electrodes, flat electrodes, percutaneous electrodes or other configurations suitable for electrical stimulation of nerves or nerve bodies or branches. In an example, the stimulation lead(s) 508 can additionally or alternatively comprise other neuromodulation therapy hardware such as the ultrasonic transducer 512, drug delivery means, or a mechanical actuator, such as can be configured to modulate neural activity.

The leads and/or electrodes discussed herein can have various features that can facilitate placement at, and stimulation of, one or more neural targets. A lead can have one or more electrodes that can be used for nerve stimulation, nerve blocking, or nerve sensing. The electrodes can have various surface area and spacing (e.g., spacing from other electrodes, sensors, targets, etc.) to optimize for a particular function. In an example, an electrode can comprise various materials, including low-oxidation metals or metal alloys (e.g., platinum, platinum iridium, etc.) for use in implantable systems. In an example, an electrode can be treated or coated with another material such as to promote healing or enhance charge transfer to tissue.

In an example, an electrode lead can comprise one or multiple electrodes, such as can having the same or different electrode characteristics. A lead can include, for example, a spiral electrode or cuff electrode. In such an example, one or more conductive surfaces can be exposed on an inside surface of a curved or spiral cuff assembly such as can comprise a portion of a lead body. In an example, a spiral cuff assembly (and hence, electrodes) can be designed to circumferentially wrap snugly around a body of a nerve and can be self-sizing. In an example, a cuff electrode can be configured to surround a particular target to thereby direct stimulation energy to the target from multiple different directions concurrently, such as while insulating the electrode from adjacent tissue.

In an example, a surface electrode or electrode array can be used. In this example, one or more electrodes can be exposed on one side of a flat or round section of a lead body. An array of electrodes of various shapes, sizes, or other characteristics, can be provided to spatially control neuromodulation therapy delivery. In an example, electrode surfaces can be oriented toward a target nerve or other structure, such as to focus an electric field provided by the electrode or electrodes. Surface electrode leads can be surgically placed by exposing the target anatomy, or can be steered using, e.g., a catheter-based delivery system from a distal surgical access point.

In an example, a percutaneous electrode can be used, such as including one or more electrodes exposed on a lead that is inserted into a blood vessel (or other conducting tissue in the vicinity of a neural target) using percutaneous techniques. A percutaneous lead can be navigated by a clinician, within or through vasculature, toward target nerves or neural structures that are in close proximity to the vasculature. In an example, electrodes on a percutaneous lead can be directly on the lead body or can comprise a percutaneous structure, such as a stent-like frame or scaffold, whereby the electrodes can be oriented towards the target and away from the blood in the vessel.

In an example, a bifurcated lead can be used to provide electrodes at multiple different and spaced apart anatomical targets while using a single connection to a header. In an example, a modular lead can be used such as to extend or tailor a lead to accommodate a patient's anatomy or target structures.

In an example, the stimulation lead(s) 508 can comprise one or more electrodes that can be provided or grouped together at a distal end of a lead, such as spaced apart from a housing, or the electrodes can be distributed along a length of the lead. In an example, a lead can include multiple different electrode groups of one or more electrodes provided at different locations along a length of the lead. Additionally, a housing of the various devices discussed herein can include one or more electrodes configured for use in electrostimulation delivery. Each of the electrodes in or coupled to the implantable system 502 can be separately addressable by neuromodulation therapy control or coordination circuitry to deliver a coordinated therapy to one or multiple targets.

Various stimulation configurations can be used with any of the electrode or lead types discussed herein. In an example, different configurations can be used to provide or modify a stimulating electric field to thereby affect an extent and manner of neural excitation. The configurations can include, for example, unipolar, bipolar, and various combinations of multipolar configurations. In a bipolar or multipolar configuration, a guard electrode can be used to help steer excitation or inhibit neural activity. In an example, an electrode configuration can be dynamically changed, such as throughout the course of a particular therapy, such as through programming changes or during operation to achieve a particular therapy.

In an example, the sensor(s) 506 can include, among other things, electrodes for sensing of electrical activity such as using electrocardiograms (ECGs), impedance, electromyograms (EMGs) of select muscles, and/or electroneurograms (ENGs) of target cranial nerves and branches. The sensor(s) 506 can include pressure sensors, photoplethysmography (PPG) sensors, chemical sensors (e.g., pH, lactate, glucose, etc.) or other sensors that can be used for physiologic sensing of cardiac, respiratory, or other physiologic activity. In an example, the sensor(s) 506 can include an accelerometer, gyroscope or geomagnetic sensor, such as can be configured to measure patient or device movement, vibration, position, or orientation information. Other examples of the sensor(s) 506 are discussed elsewhere herein, including in the discussion of the machine 1700 and the various I/O components 1742, such as including the biometric components 1732, motion components 1734, and environmental components 1736. In an example, information from the sensor(s) 506 can be received by the processor circuit 510 and used to update or titrate a neuromodulation therapy.

In an example, the implantable system 502 can include one or more sensor(s) 506, such as can be used in providing closed-loop neuromodulation therapy that is based at least in part on physiologic status information about a patient (e.g., respiration, heart rate, blood pressure, neural or muscular activation, or other information). In an example, the sensor(s) 506 can be used to receive diagnostic information, or to receive information about patient movement or body position.

In an example, hypoglossal nerve stimulation, such as to treat OSA, can be controlled at least in part based on information from an accelerometer or gyroscope to determine patient respiration, patient activity, and body orientation or position, such as together with information from a pressure sensor about respiration. In other words, using information from the sensor(s) 506, such as including accelerometer and pressure sensors, the implantable system 502 can control neuromodulation therapy provided to the hypoglossal nerve, such as can include stimulation during a particular time within a respiratory cycle, and can use body position information to automatically enable therapy when, for example, the patient is sleeping.

In the example of FIG. 5, the external system 520 can include various components that can be provided together as a unitary external device or can include multiple devices configured to work together to manage a patient therapy, manage a device such as the implantable system 502, or perform other functions associated with the implantable system 502. The external system 520 can include an antenna 522, a processor circuit 524, and an interface 526, among other components or modules.

The antenna 522 can comprise one or multiple antennas such as can be configured for nearfield or farfield communications with, for example, the antenna 504 of the implantable system 502, a different implantable device or system, or other external device. In an example, the antenna 522 and the antenna 504 can be used to exchange power or data between the implantable system 502 and the external system 520. For example, information about a prescribed therapy can be uploaded from the external system 520 to the implantable system 502, or information about a physiologic status, such as measured by the sensor(s) 506, can be downloaded from the implantable system 502 to the external system 520.

The processor circuit 524 can include a general purpose or purpose-built processor configured to carry out various activities on the external system 520 or in coordination with the implantable system 502. In an example, the processor circuit 524 of the external system 520 is configured to manage telemetry or data signal communications with the implantable system 502, such as using the antenna 522 or other communication circuitry.

The interface 526 can include a patient or clinician interface, such as to report device information or to receive instructions or therapy parameters for implementation by the implantable system 502. In an example, the interface 526 can include an interface or gateway to facilitate communication between the 502 or the external system 520 with a patient management system or other medical record system. Other features, modules, and components of the implantable system 502 and the external system 520 can be included in the system 500 to help administer various neuromodulation therapies.

In an example, the systems, devices, and components discussed herein, including at least the implantable system 502 and the external system 520 of the system 500, can be used to provide neuromodulation therapy to nerve targets inside a patient body, such as to treat one or more disorders or diseases. In an example, the system 500 or components thereof can be configured to provide neuromodulation therapy to multiple nerve targets in a coordinated manner, such as concurrently, or in a time-multiplexed sequence. In an example, the neuromodulation therapy can include one or more, or combinations of, neural stimulation and blocking signals, such as can be directed to afferent or efferent nerve structures or targets to trigger different responses. The therapy can optionally include using vector-based stimulation configurations to target particular nerves or nerve regions, or can include more relatively targeted or isolated nerve fibers. In an example, a coordinated neuromodulation therapy can include blocking at a first nerve target, while stimulating a second nerve target, or concurrently (or in time-sequence) stimulating multiple different nerve targets.

In an example, the particular patient disorder or disease can dictate the particular neural target to modulate with a neuromodulation therapy. For example, to treat obstructive sleep apnea using the system 500, various cranial nerves can be targeted individually or together, such as including the trigeminal nerve (e.g., the V3 mandibular branch of the trigeminal nerve 428), the hypoglossal nerve 418 (e.g., including one or more branches thereof), the glossopharyngeal nerve 412, the vagus nerve 416, or the facial nerve 402 (e.g., including various extracranial branches thereof).

In an example, the system 500 can be used to treat OSA by providing a neuromodulation therapy to or including the mandibular branch of the trigeminal nerve 428 and the hypoglossal nerve 418. In this example, neuromodulation of the mandibular branch of the trigeminal nerve 428 can influence motor control of the mylohyoid muscle 114 or the anterior digastric muscle 204, and neuromodulation of the hypoglossal nerve 418 can influence motor control of muscles in the tongue 406.

In an example, the system 500 can be used to treat OSA by providing a neuromodulation therapy to or including the facial nerve 402 and to the hypoglossal nerve 418. In this example, neuromodulation of the facial nerve 402 can influence motor control of the stylohyoid muscle 304 or the posterior digastric muscle 208, and neuromodulation of the hypoglossal nerve 418 can influence motor control of muscles in the tongue 406.

In an example, the system 500 can be used to treat OSA by providing a neuromodulation therapy to or including the glossopharyngeal nerve 412 and the hypoglossal nerve 418. In this example, neuromodulation of the glossopharyngeal nerve 412 can influence motor control of the stylopharyngeus muscle, and neuromodulation of the hypoglossal nerve 418 can influence motor control of muscles in the tongue 406.

In an example, the system 500 can be used to treat OSA by providing a neuromodulation therapy to or including various branches of the hypoglossal nerve 418, including anterior branches, posterior branches, or multiple branches concurrently, including or using a bilateral configuration to target branches on opposite sides of the midline 102 of a patient. The neuromodulation of the hypoglossal nerve 418 can influence motor control of various muscles in the tongue 406. In an example, neuromodulation therapy that includes stimulating or blocking the hypoglossal nerve 418 can be combined with therapy that targets one or more of the mandibular branch of the trigeminal nerve 428 (e.g., to influence motor control of the mylohyoid muscle 114 or the anterior digastric muscle 204), the facial nerve 402 (e.g., to influence motor control of the stylohyoid muscle 304 or the posterior digastric muscle 208), or the glossopharyngeal nerve 412 (e.g., to influence motor control of the stylopharyngeus muscle), among others.

Any one or more branches of the hypoglossal nerve 418 can receive a neuromodulation therapy from the implantable system 502. For example, any one or more of the posterior branches of the hypoglossal nerve 418 can receive neuromodulation, including for example "branches" off the hypoglossal nerve sheath such as the descending branch, also referred to as the superior root of the ansa cervacalis, the thyrohyoid branch, or the geniohyoid branch. Any one or more of the anterior branches of the hypoglossal nerve 418 can receive neuromodulation, including for example where a main trunk of the hypoglossal nerve 418 branches to the muscles of the tongue, also referred to as the muscular branch (B6), or including the muscular branch itself. The muscular branch can include sub-branches or nerve fibers that innervate specific muscles of the tongue.

In an example, the system 500 can be used to treat OSA or other disorders or diseases such as heart failure, hypertension, atrial fibrillation, epilepsy, depression, stroke, autism, inflammatory bowel disease, chronic inflammation, chronic pain (e.g., in cervical regions, in the lower back, or elsewhere), tinnitus, or rheumatoid arthritis, among others, such as by providing a neuromodulation therapy to or including the vagus nerve 416. Neuromodulation of the vagus nerve 416 can influence parasympathetic tone to thereby treat or alleviate symptoms associated with the various diseases or disorders mentioned, among others. In an example, a therapy that includes stimulation of the vagus nerve 416 can include therapy provided to one or more branches of the hypoglossal nerve 418, the mandibular branch of the trigeminal nerve 428, the facial nerve 402, or the glossopharyngeal nerve 412. In an example, neuromodulation therapy that includes stimulating or blocking a portion of the vagus nerve 416 can be combined with therapy that targets one or more of the glossopharyngeal nerve 412 (e.g., to further influence parasympathetic tone), the carotid sinus (e.g., to stimulate a baroreceptor response), or the superior cervical ganglion or branches thereof (e.g., to influence sympathetic tone).

In an example, a neuromodulation therapy for treatment of heart failure, hypertension, and/or atrial fibrillation can include therapy provided to or including one or more of the glossopharyngeal nerve 412 (e.g., to influence parasympathetic tone, such as via communication to the vagus nerve 416), the superior cervical ganglion (e.g., to influence sympathetic tone), or the carotid sinus (e.g., to stimulate a baroreceptor response).

In an example, the system 500 can be configured to treat heart failure, hypertension, migraine headaches, xerostomia, or other diseases or disorders by providing a neuromodulation therapy to or including the glossopharyngeal nerve 412. Stimulation or blocking of the glossopharyngeal nerve 412 can, for example, influence parasympathetic tone or can affect motor activity of the stylopharyngeus muscle.

In an example, the system 500 can be configured to treat drug-refractory epilepsy, depression, post-traumatic stress disorder (PTSD), migraine headaches, attention-deficit hyperactivity disorder (ADHD), craniofacial pain syndrome, among other diseases and disorders, such as by providing a neuromodulation therapy to or including the mandibular branch of the trigeminal nerve 428.

In an example, the system 500 can be configured to treat craniofacial pain syndrome, or facial palsy, among other things, such as by providing a neuromodulation therapy to or including the facial nerve 402, such as including various extracranial branches or roots thereof. In an example, the system 500 can be configured to treat fibromyalgia such as by providing a neuromodulation therapy to or including the spinal accessory nerve, such as to target the trapezius muscle, which is understood to be a potential trigger point for fibromyalgia. In an example, the system 500 can be configured to treat migraine headaches or tinnitus, such as by providing a neuromodulation therapy to or including a great occipital nerve, such as can be accessed using electrodes implanted in the cervical region of a patient.

Neuromodulation therapies can thus be provided using the system 500, or using components thereof, to treat a variety of different diseases or disorders. The therapies can include targeted, single-location stimulation or blocking (e.g., using electrical pulses, ultrasonic signals, or other energy) therapy at one of the locations mentioned herein (among others) or can include coordinated stimulation or blocking across or using multiple different locations. The following discussion illustrates several examples of different implantation locations and neural targets, however, others including those specifically mentioned above, can similarly be used.

In an example, the implantable system 502 can comprise various devices that can be implanted in various different areas of the body, including in a cervical region. The examples of FIG. 3, and FIG. 6 through FIG. 13, illustrate generally different examples of the implantable system 502 such as implanted in various different cervical locations.

Figure 6:
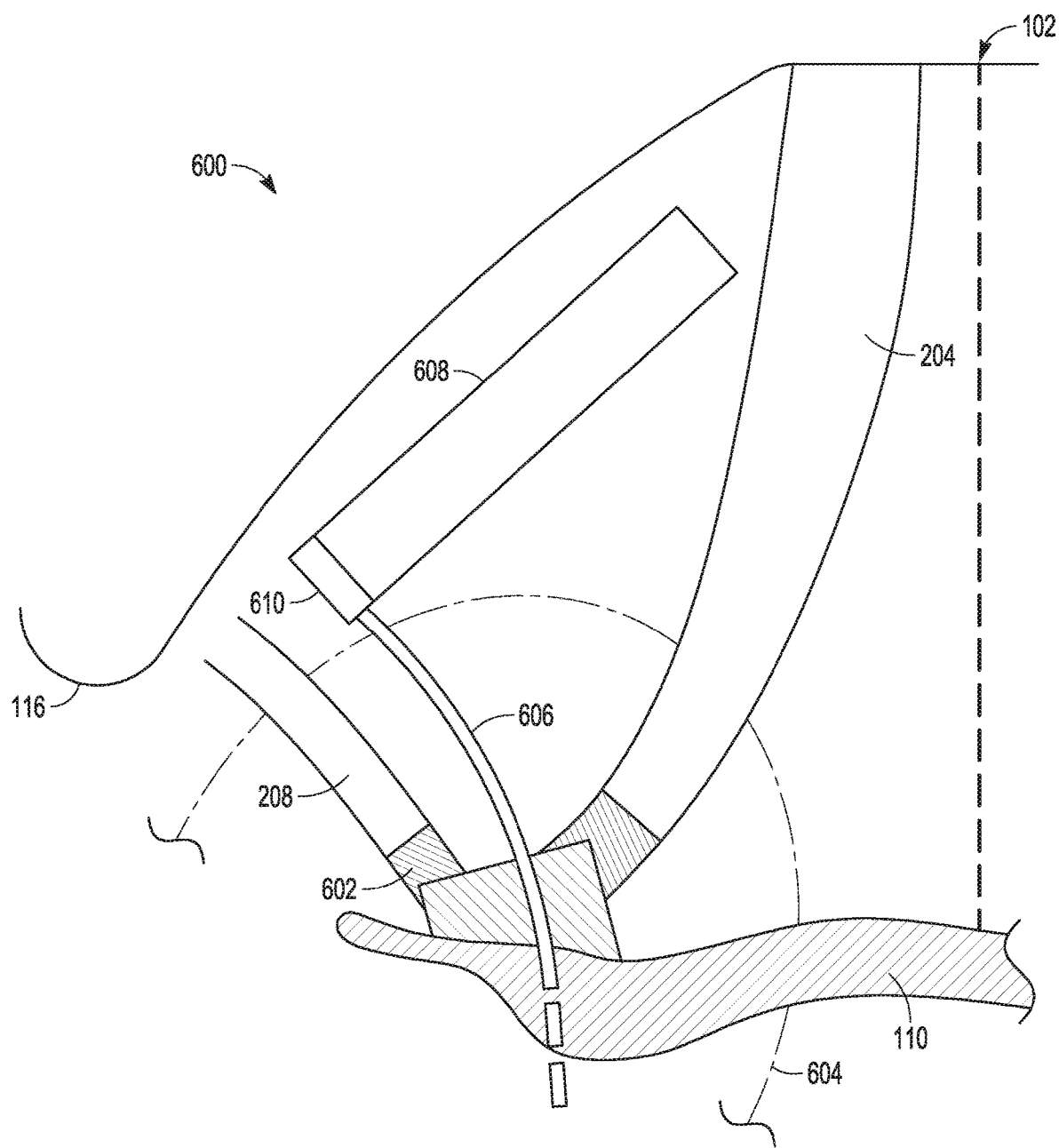
FIG. 6 illustrates generally a first implantable device implanted in a submandibular triangle of a patient.

FIG. 6 illustrates generally a first example 600 that includes a first implantable device 608 implanted in the submandibular triangle 206 of a patient. In the first example 600, the first implantable device 608 can be coupled to an anatomic structure in the submandibular triangle 206, such as using a suture, anchor, or other affixation means. In an example, the first implantable device 608 can be coupled to one or more of the mandible 116, the anterior digastric muscle 204, the posterior digastric muscle 208, the mylohyoid muscle 114, the digastric tendon 602, or other bone, tendon, muscle, or other structure that is in or adjacent to the submandibular triangle 206. In the example of FIG. 6, the first implantable device 608 can be provided near, but spaced apart from, a submandibular gland 604 of the patient.

In the example of FIG. 6, the first implantable device 608 includes a first header 610. The first header 610 can be used to couple one or multiple electrode leads, sensor leads, or other devices to the first implantable device 608. For example, the first header 610 can be used to couple the first implantable device 608 to a first electrode lead 606, and the first electrode lead 606 can be tunneled to a cranial nerve target. Electrodes configured to deliver electrostimulation signals to the nerve target can be situated at or adjacent to the target. In an example, the first electrode lead 606 can be tunneled to a hypoglossal nerve in or near an anterior cervical region of a patient.

In the example of FIG. 6, the first implantable device 608 is shown with one header. The first implantable device 608 can optionally include multiple headers to interface the first implantable device 608 with one or multiple other leads, such as electrode leads, sensor leads, communication coils, or other devices. Referring again to FIG. 4, for example, the implantable therapy device 426 can include multiple headers, such as coupled to the respective different leads that extend from opposite sides of a body of the implantable therapy device 426.

Figure 7:
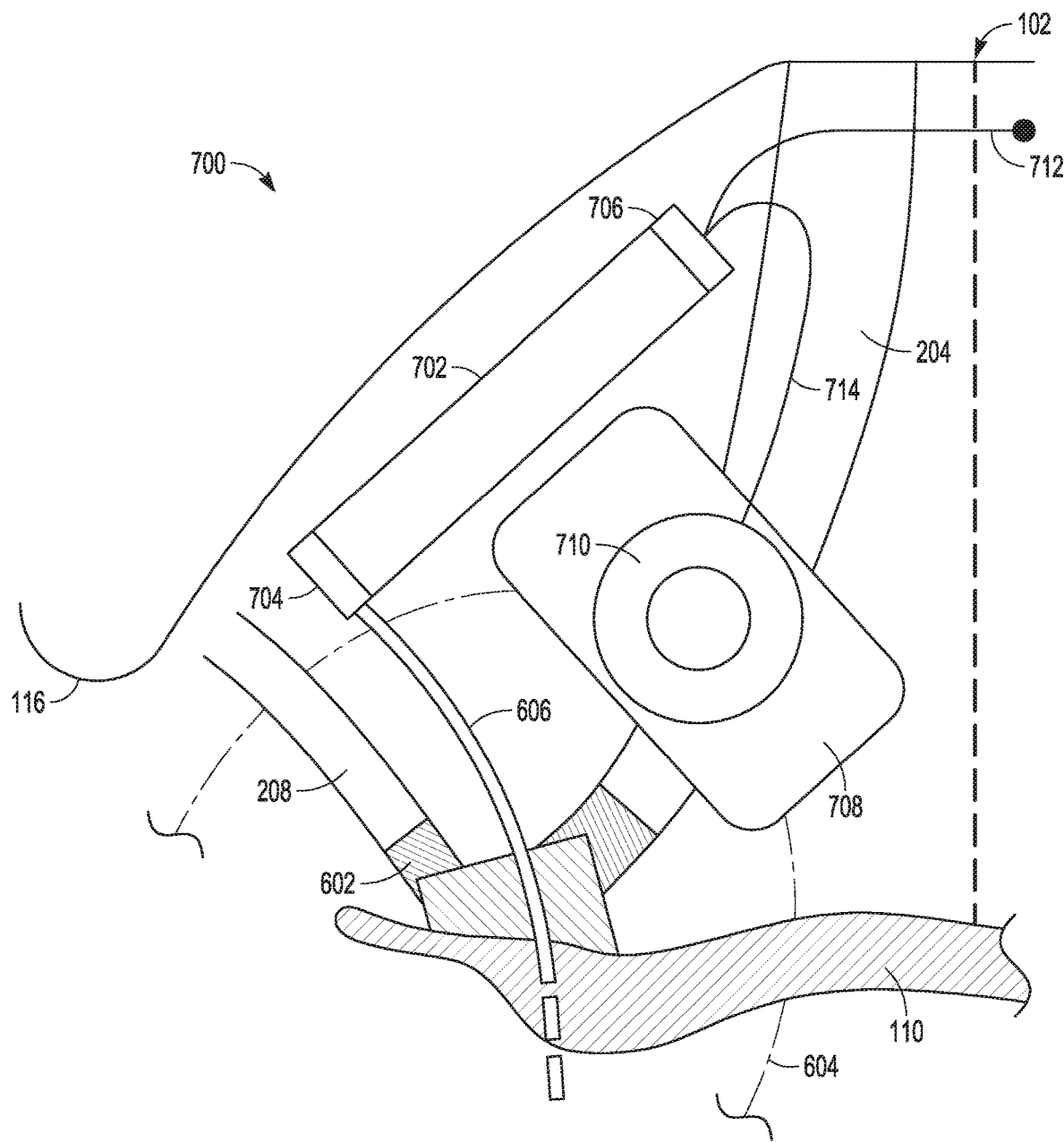
FIG. 7 illustrates generally a second implantable device implanted in a submandibular triangle of a patient.

FIG. 7 illustrates generally a second example 700 that includes a second implantable device 702 implanted in the submandibular triangle 206 of a patient. In the second example 700, the second implantable device 702 can be coupled to an anatomic structure in the submandibular triangle 206, such as using a suture, anchor, or other affixation means. In an example, the second implantable device 702 can be coupled to one or more of the mandible 116, the anterior digastric muscle 204, the posterior digastric muscle 208, the mylohyoid muscle 114, or other bone, tendon, muscle, or other structure that is in or adjacent to the submandibular triangle 206.

The example of the second implantable device 702 includes an elongate housing structure with respective headers on opposite side ends of the device. For example, the second implantable device 702 includes a first header 704 coupled to the first electrode lead 606, such as can be tunneled to a first cranial nerve target. The second implantable device 702 can include a second header 706 coupled to a second electrode lead 712 and to a first data and power communication lead 714. The second electrode lead 712 can be coupled to a second cranial nerve target.

In an example, the first data and power communication lead 714 can couple the second implantable device 702 to a wireless communication coil 710. The wireless communication coil 710 can be configured to facilitate data or power signal communication with a wireless external device, such as external to the patient. In an example, the wireless communication coil 710 comprises the antenna 504 that can be used to communicate with the external system 520. Power or data signals received using the wireless communication coil 710 can be communicated to the second implantable device 702 and stored or used.

In the example of FIG. 7, the wireless communication coil 710 can be coupled or mounted to a first coil support 708. The first coil support 708 and the wireless communication coil 710 can comprise a flexible structure that can be positioned at or near a tissue interface of a patient, such as under the skin and adjacent to muscle, bone, or other tissue. For example, the first coil support 708 can be provided at or adjacent to a surface of the anterior digastric muscle 204 and facing away from the patient body. In another example, the first coil support 708 can be provided interiorly to the anterior digastric muscle 204, or behind the anterior digastric muscle 204 in the view of FIG. 7. The first coil support 708 can be otherwise oriented elsewhere in the anterior triangle 104 of the patient and can be coupled to the second implantable device 702 by tunneling the first data and power communication lead 714. For example, the first coil support 708 can be provided under a chin region, such as at or near a tip of the submental triangle 202 of the patient, away from the hyoid bone 110.

Figure 8:
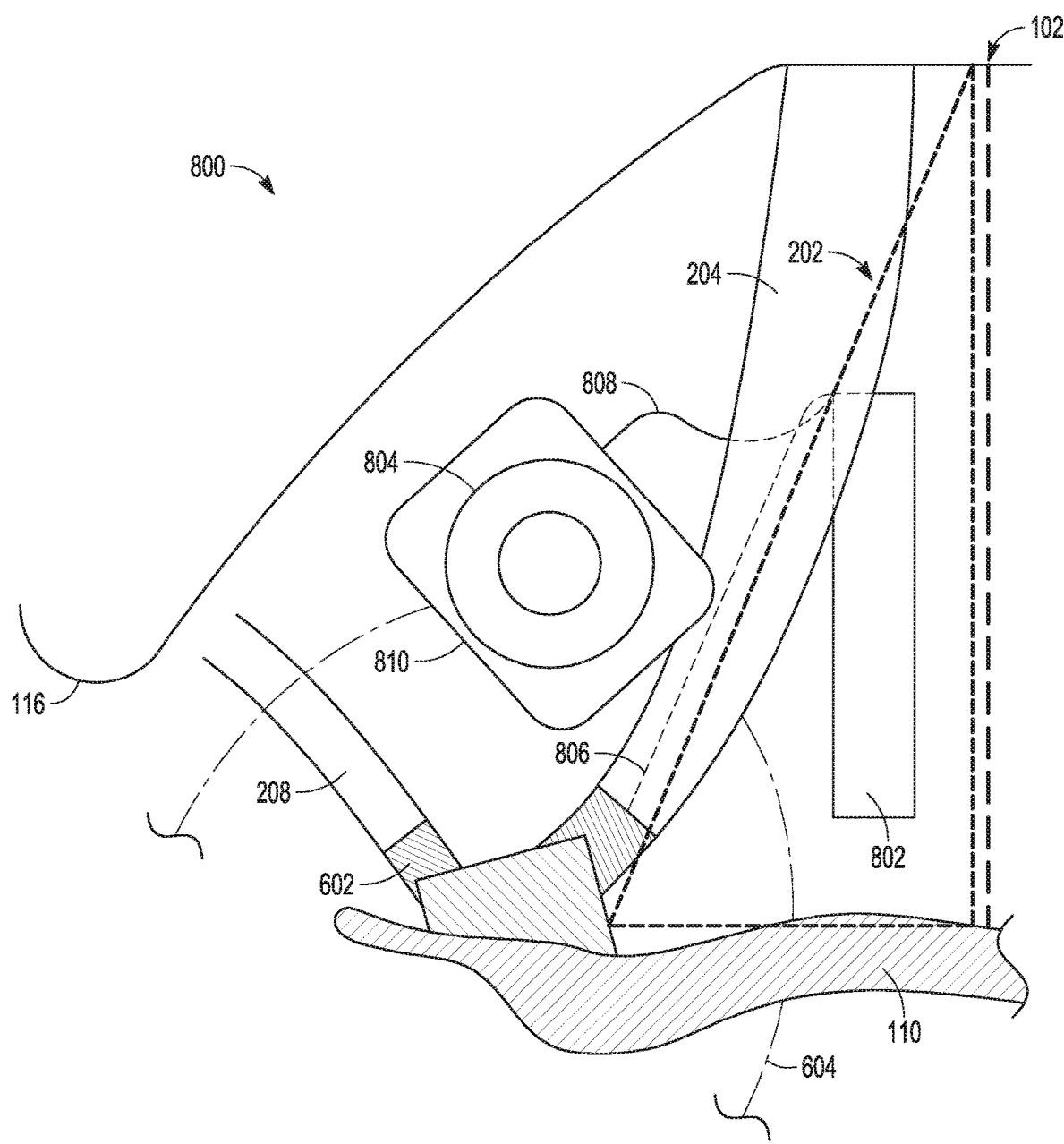
FIG. 8 illustrates generally an example that includes a submental implantable device implanted in a submental triangle of a patient.

FIG. 8 illustrates generally a third example 800 that includes a submental implantable device 802 implanted in the submental triangle 202 of a patient. In the third example 800, the submental implantable device 802 can be coupled to an anatomic structure in the submental triangle 202, such as using a suture, anchor, or other affixation means. In an example, the submental implantable device 802 can be coupled to one or more of the mylohyoid muscle 114, the anterior digastric muscle 204, the hyoid bone 110, or other bone, tendon, muscle, or other structure that is in or adjacent the submental triangle 202. The submental implantable device 802 can be installed adjacent to, or at least partially under the anterior digastric muscle 204, such as between the anterior digastric muscle 204 and the underlying mylohyoid muscle 114.

The example of the submental implantable device 802 includes an elongate housing structure with at least one header on a first side end of the device. In the example of FIG. 8, the submental implantable device 802 is coupled to an electrode lead 806 that can be tunneled to a first cranial nerve target. The submental implantable device 802 can be coupled to a submandibular communication coil 804, such as using a second data and power communication lead 808.

In the example of FIG. 8, the submandibular communication coil 804 can be coupled or mounted to a second coil support 810. The second coil support 810 and the submandibular communication coil 804 can comprise a flexible structure that can be positioned at or near a tissue interface of a patient, such as under the skin and adjacent to muscle, bone, or other tissue. For example, the second coil support 810 can be provided at or adjacent to a surface of at least one of the posterior digastric muscle 208 and the anterior digastric muscle 204, and can be oriented such that the submandibular communication coil 804 faces away from the patient body, in another example, the first coil support 708 can be provided interiorly to the digastric muscles, such as adjacent to the mylohyoid muscle 114.

Figure 9:
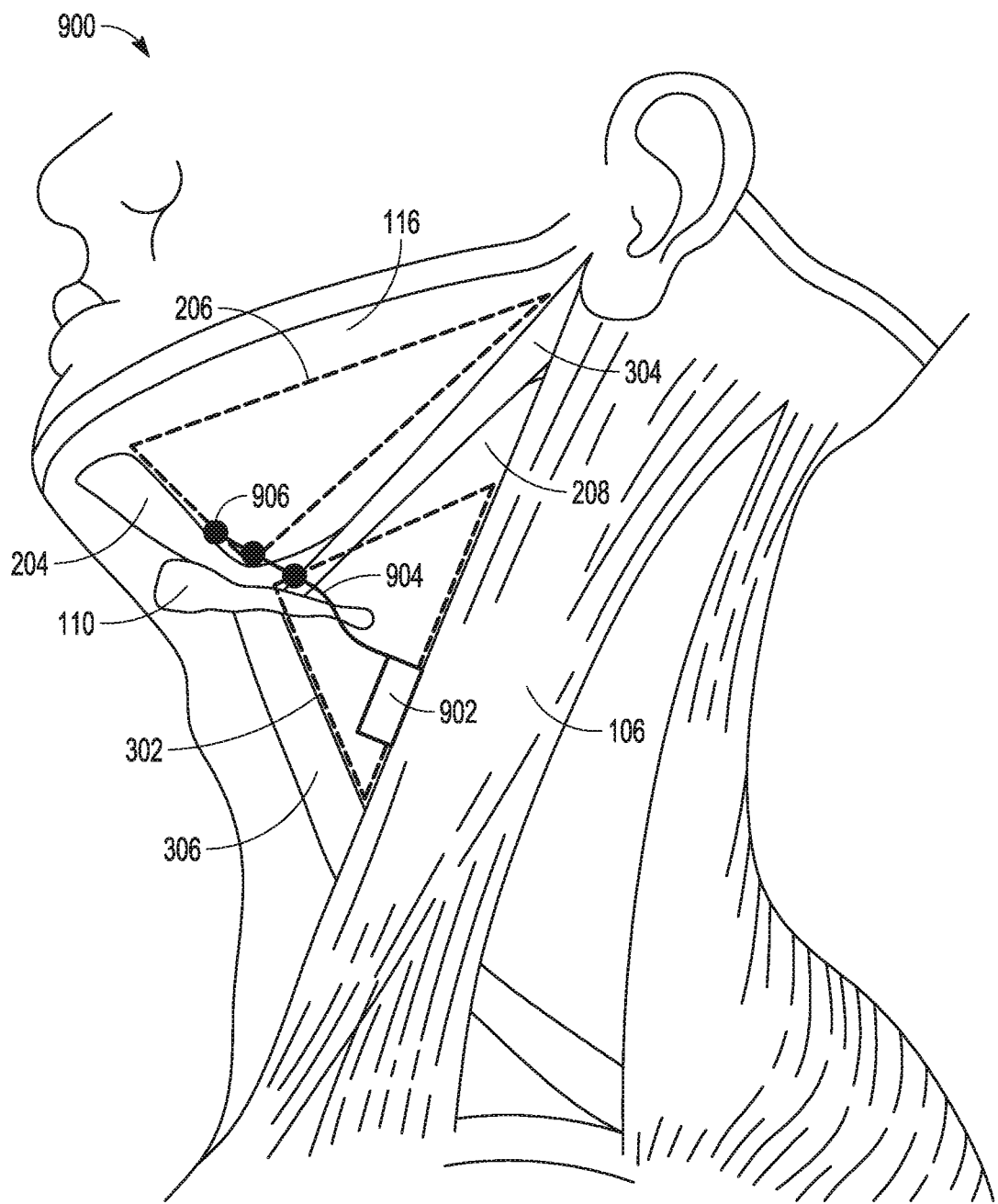
FIG. 9 illustrates generally an example of a third implantable device implanted in a carotid triangle of a patient.

FIG. 9 illustrates generally a fourth example 900 that includes a third implantable device 902 implanted in the carotid triangle 302 of a patient. In the fourth example 900, the third implantable device 902 can be coupled to an anatomic structure in the carotid triangle 302, such as using a suture, anchor, or other affixation means. In an example, the third implantable device 902 can be coupled to one or more of the SCM 106, the omohyoid muscle 306, the hyoid bone 110, or other bone, tendon, muscle, or other structure that is in or adjacent to the carotid triangle 302.

The example of the third implantable device 902 includes an elongate housing structure with at least one header on a first side end of the device. In the example of FIG. 9, the third implantable device 902 is coupled to a multipolar electrode lead 904 that can be tunneled to a cranial nerve target. For example, an electrode array 906 of the multipolar electrode lead 904 can be disposed at or near a nerve target (or targets) outside of the carotid triangle 302, and the multipolar electrode lead 904 can be tunneled to the carotid triangle 302 to couple with the third implantable device 902. In an example, the electrode array 906 can be provided at or near a hypoglossal nerve 418 of the patient, such as in or near the submandibular triangle 206.

Figure 10:
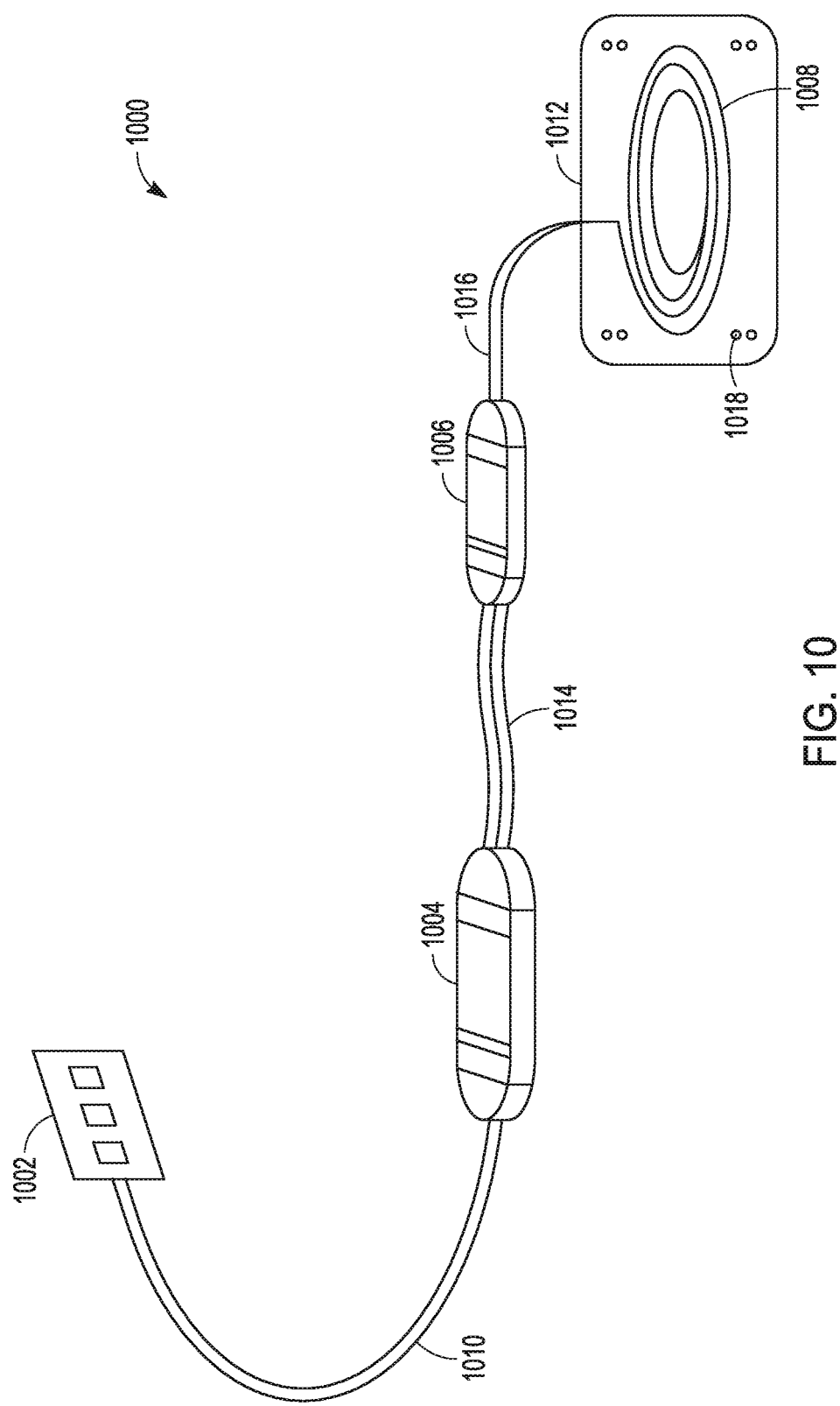
FIG. 10 illustrates generally an example of a first segmented implantable device.

FIG. 10 illustrates generally an example of a first segmented device 1000. The first segmented device 1000 can be an implantable device that is configured for implantation at or in an anterior cervical region of a patient. For example, the first segmented device 1000 can be configured to be implanted in one or multiple different triangles of the cervical region, as further described below. That is, different segments or portions of the first segmented device 1000 can be implanted in respective different triangles in a cervical region of a patient. In an example, the first segmented device 1000 comprises the implantable system 502 from the example of FIG. 5.

The first segmented device 1000 includes a first housing 1004 and a second housing 1006 that can be connected using a flexible housing coupling 1014. The first segmented device 1000 can include a first cuff electrode 1002 (e.g., comprising one or multiple electrodes) that is coupled to the first housing 1004 using an electrode lead 1010. The first segmented device 1000 can further include a communication coil 1008, such as can be electrically coupled to the second housing 1006 using a power and data lead 1016.

The communication coil 1008 can be coupled to a support member 1012 that can help maintain the coil in a configuration suitable for wireless communications with an external transmitter. In an example, the support member 1012 can include one or more mounting features 1018 to couple the support member 1012, and therefore the communication coil 1008, to an anatomical structure inside a patient body. For example, the mounting feature 1018 can include one or more through-holes in the support member 1012 that can be used to suture the support member 1012 to a tissue site. In an example, the support member 1012 can comprise a flexible, irregularly shaped flap configured for implantation and avoidance of particular structures, such as a submandibular gland or nerve to the mylohyoid. The flap can help couple the support member 1012 superiorly.

In an example, the second housing 1006 comprises a power storage circuit, such as can comprise the power storage circuit 514 from the example of FIG. 5. The power storage circuit can comprise a battery, a capacitor bank, or other means to store electrical power, such as can be received wirelessly using the communication coil 1008.

In an example, the various leads and couplings that comprise the first segmented device 1000 can include one or more electrical conductors. Power signals, electrostimulation signals, or other signals can be communicated among the different portions of the first segmented device 1000 using the electrical conductors. For example, the housing coupling 1014 can include a power conductor such that a battery in the second housing 1006 can be used to power electrostimulation control circuitry in the first housing 1004.

In an example, the first segmented device 1000 can comprise component parts that can be organized in various different configurations, such as to optimize implantation or to configure the device to best match a particular patient anatomy. That is, the device can be configured to accommodate anatomic variations among different patients. For example, different lead lengths can be selected, or the orientation or position of the different components along the signal chain can be adjusted.

In an example, the first housing 1004 or the second housing 1006 can use headers to connect with the various leads, or the first housing 1004 and the second housing 1006 can be integrated (e.g., attached at a point of manufacture rather than at a time of implantation) with their respective leads. By using a modular approach, component parts can be surgically updated or upgraded.

In an example, respective portions of the first segmented device 1000 can be configured for implantation in submandibular triangle 206 and in the submental triangle 202 of a patient. That is, the first segmented device 1000 can be configured to extend between the triangle regions, such as across a portion of a digastric muscle. Providing the portions of the first segmented device 1000 in different triangles of the cervical region can help minimize interference between the first segmented device 1000 and patient movement, such as due to activity of the digastric muscles. In an example, the first housing 1004 and the second housing 1006 can be differently sized such that a larger of the two housings can be disposed in the particular triangular region that offers more space. Such a distributed arrangement or implantation of the components of the first segmented device 1000 can be helpful in maintaining patient comfort since muscles in the cervical region can be used for complex movement of the head, neck, mouth, tongue, and other areas.

Figure 11:
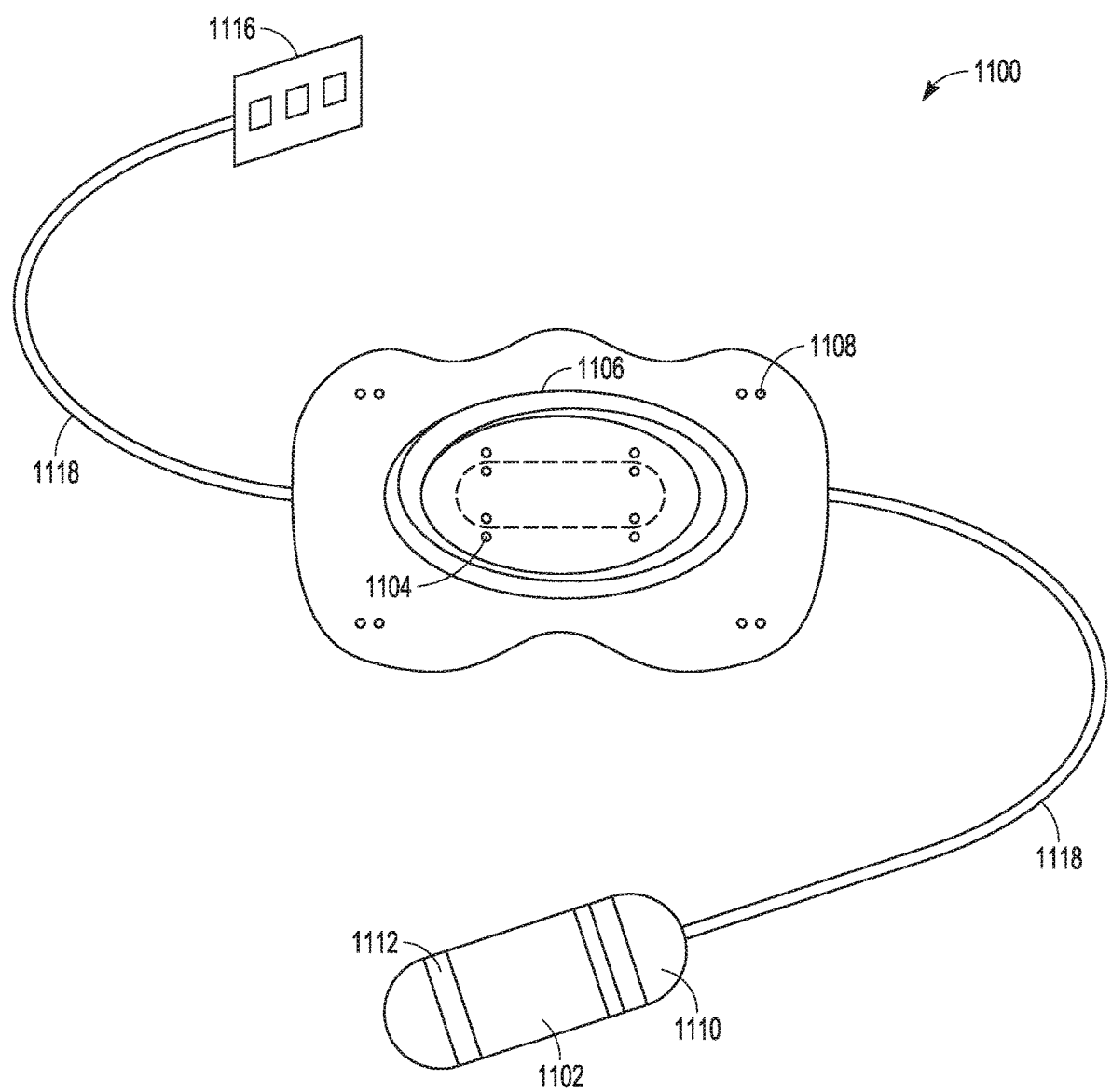
FIG. 11 illustrates generally an example of a submandibular implantable device.

FIG. 11 illustrates generally an example of a submandibular implantable device 1100. The submandibular implantable device 1100 can be an implantable device that is configured for implantation at or in an anterior cervical region of a patient. For example, the submandibular implantable device 1100 can be configured to be implanted in one or multiple different triangles of the cervical region, as further described below, That is, different segments or portions of the submandibular implantable device 1100 can be implanted in the same triangle region or in respective different triangle regions in a cervical region of a patient.

The submandibular implantable device 1100 includes an implantable device housing 1102 that can include, among other things, power storage circuitry, electrostimulation generation circuitry, and control circuitry. Circuitry in the implantable device housing 1102 can be coupled to an electrode assembly 1116 using a power, data, and therapy signal lead 1118, and the electrode assembly 1116 can be used to provide neuromodulation signals at a cervical neural target in a patient body. In an example, the circuitry in the implantable device housing 1102 can be coupled to the electrode assembly 1116 via a device header 1110.

In an example, the implantable device housing 1102 can be coupled to a communication coil 1106 using one or more conductors in the power, data, and therapy signal lead 1118. The communication coil can include a power communication coil and/or a telemetry antenna. In an example, the communication coil 1106 can be coupled to a support member 1114. The support member 1114 can include one or more support mounting features 1108 for coupling the support member 1114 to tissue. In an example, the support member 1114 can include a housing mount 1104 that is configured to receive or couple with the implantable device housing 1102, That is, the support member 1114 can include a mounting structure or feature that can be configured to secure or retain the implantable device housing 1102 together with the support member 1114. In an example, the implantable device housing 1102 can include various features that are configured to mate with, or to be used together with, the housing mount 1104. For example, the housing mount 1104 can include suture holes, and the device mounting feature 1112 can comprise a through-hole or groove that is configured to receive a suture therein. A suture can then be used to join the implantable device housing 1102 to the support member 1114 using the housing mount 1104. In an example, the support member 1114 can be configured to be coupled or otherwise affixed to the mylohyoid muscle 114, such as in or near the submental triangle 202 or the submandibular triangle 206 of a patient.

In an example, the device mounting feature 1112 can be configured to receive one or more sutures, bands, or flaps that are configured to loop around structures like a digastric tendon or a hyoid bone or other connective tissue, and can affix back to itself, thereby coupling the implantable device housing 1102 to a stable piece of the anatomy.

Figure 12:
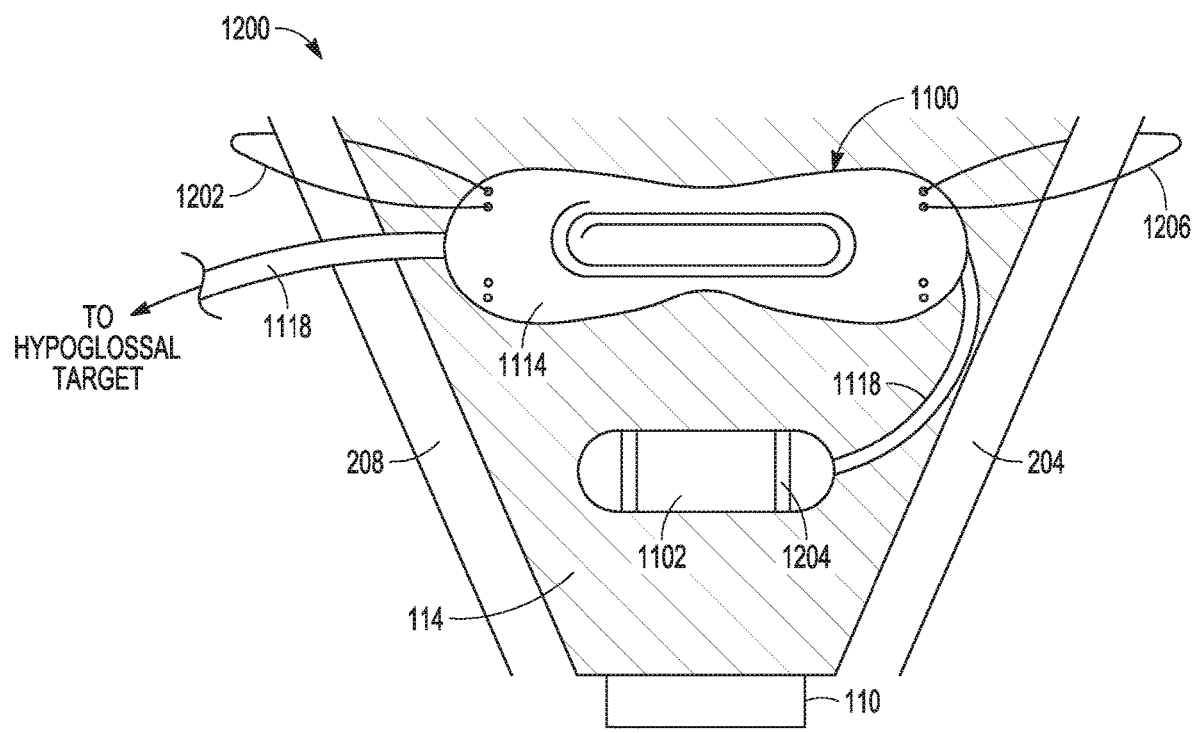
FIG. 12 illustrates generally an example of a device implanted in a submandibular triangle region of a patient.

FIG. 12 illustrates generally a first submandibular triangle example 1200 that can include or use the submandibular implantable device 1100 from the example of FIG. 11. In the example, portions of the submandibular implantable device 1100 can be implanted in a submandibular triangle region of a neck, such as between the anterior digastric muscle 204 and the posterior digastric muscle 208.

In the example of FIG. 12, the support member 1114 of the submandibular implantable device 1100 can be coupled to one or more anatomic structures in the submandibular triangle. For example, the support member 1114 can be coupled to the anterior digastric muscle 204 using an anterior suture 1206, or to the posterior digastric muscle 208 using a posterior suture 1202, or to the mylohyoid muscle 114, such as using one or more other sutures.

The implantable device housing 1102 can be coupled to the same digastric structures as the support member 1114, or can be coupled to other anatomic structures in the submandibular triangle. For example, the implantable device housing 1102 can be coupled to the mylohyoid muscle 114, such as using a housing-tissue anchor 1204. In an example, the housing-tissue anchor 1204 can include one or more sutures that can wrap around or through a portion of the implantable device housing 1102 and the muscle tissue, to thereby affix the housing-tissue anchor 1204 to tissue inside the submandibular triangle.

Figure 13:
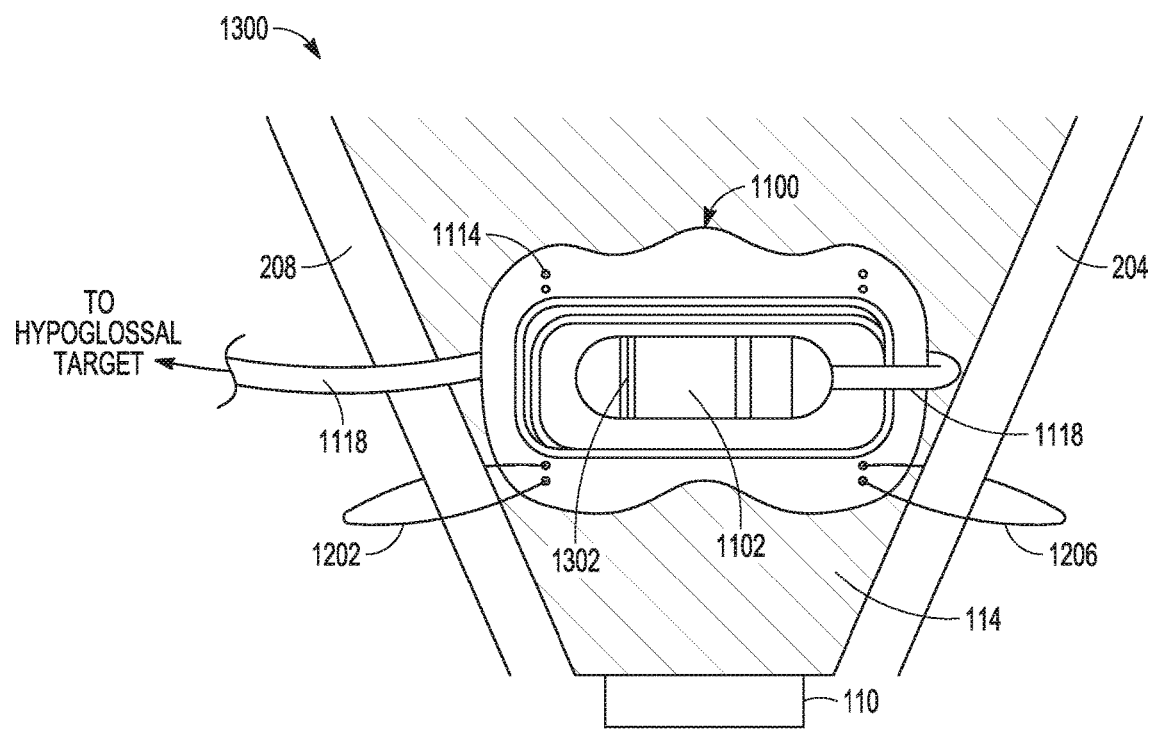
FIG. 13 illustrates generally an example of a device implanted in a submandibular triangle region of a patient.

FIG. 13 illustrates generally a second submandibular triangle example 1300 that can include or use the submandibular implantable device 1100 from the example of FIG. 11. In the example, the implantable device housing 1102 can be coupled to the support member 1114, such as using the housing mount 1104. The assembly that includes the support member 1114 and the implantable device housing 1102 can be implanted in a submandibular triangle region of a neck, such as between the anterior digastric muscle 204 and the posterior digastric muscle 208. In an example, the support mounting features 1108 of the support member 1114 can be used to couple respective sides of the assembly to the anterior digastric muscle 204 and the posterior digastric muscle 208.

The example of FIG. 13 illustrates the implantable device housing 1102 coupled to an outward-facing first surface of the support member 1114. That is, FIG. 13 shows the implantable device housing 1102 facing toward skin or away from other internal cervical structures. In an example, the implantable device housing 1102 can be coupled to an opposite second surface of the support member 1114, such as facing inward toward the mylohyoid muscle 114 and other internal cervical structures. The implantable device housing 1102 can be coupled to the support member 1114 using, for example, a housing-support anchor 1302, such as can include a suture, clip, cuff, or other means for coupling a flexible support substrate of the support member 1114 to a structural housing.

Figure 14:
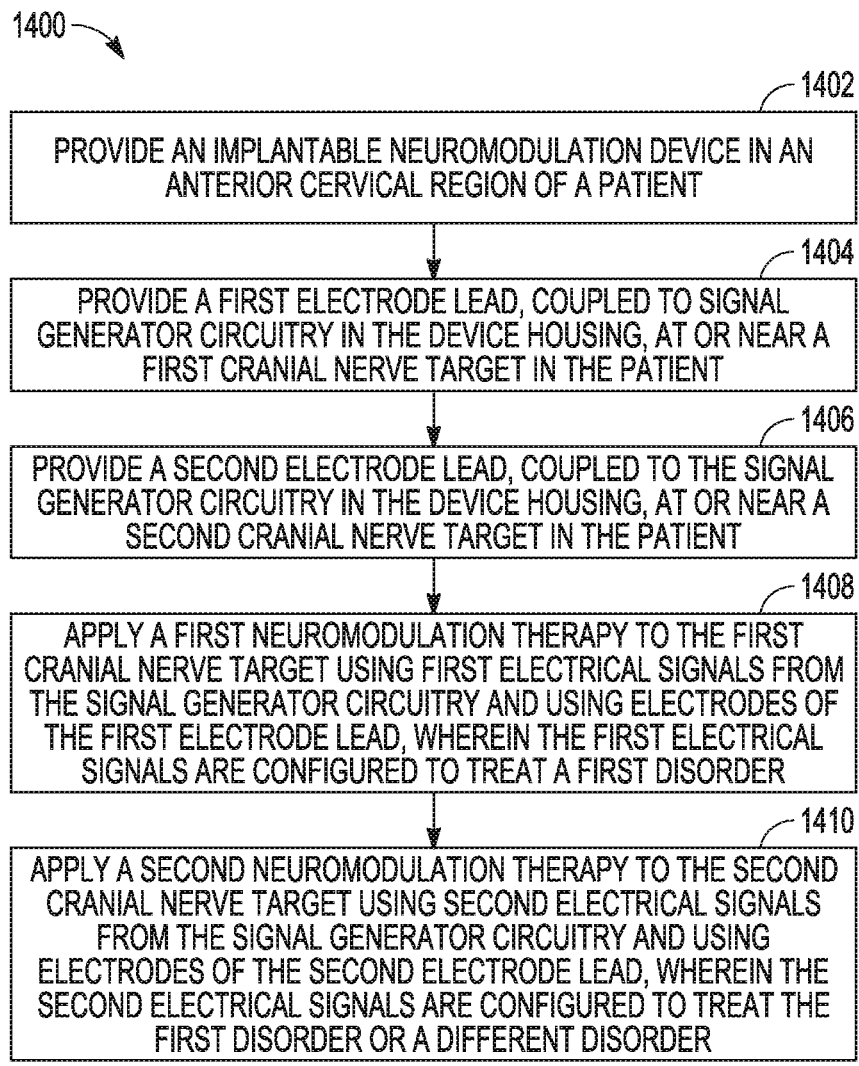
FIG. 14 illustrates a method for treating a patient disorder using a neuromodulation system.

The examples of FIG. 12 and FIG. 13 illustrate generally the submandibular implantable device 1100 with the power, data, and therapy signal lead 1118 extending away from the submandibular triangle to a hypoglossal nerve target. One or more other nerve targets can similarly be accessed using one or more other leads, such as using the same support member 1114 and implantable device housing 1102 and circuitry therein, FIG. 14 illustrates generally an example of a method 1400 that can include providing a neuromodulation therapy to multiple cranial nerves. The method 1400 can optionally include or use the system 500 or other system configured for modulation of a nerve stimulation or blocking therapy.

At block 1402, the method 1400 can include providing an implantable neuromodulation device in an anterior cervical region of a patient. For example, block 1402 can include implanting the implantable system 502 (or one or more components thereof) in one or more of the submental triangle 202, the submandibular triangle 206, or the carotid triangle 302 in an anterior portion of a patient neck. In an example, block 1402 can include implanting or coupling multiple different housings that comprise portions of the system 500 to various anatomic structures that are in or that border the various triangle regions in the anterior portion of the patient neck.

At block 1404, the method 1400 can include providing a first lead, such as an electrode lead (e.g., a first instance of a stimulation lead(s) 508), at or near a first cranial nerve target in the patient. Block 1404 can include coupling the electrode lead to signal generator circuitry in a housing such as implanted with the neuromodulation device at block 1402. In an example, block 1404 can include implanting a lead with electrodes that are disposed at or near one or more of the hypoglossal nerve 418, the glossopharyngeal nerve 412, the facial nerve 402, the mandibular branch of the trigeminal nerve 428, the vagus nerve 416, or elsewhere in or near the head or neck of the patient. In an example, the method 1400 can include, at block 1406, providing a second lead, such as an electrode lead (e.g., a second instance of a stimulation lead(s) 508), at or near a second cranial nerve target in the patient. Block 1406 can include coupling the electrode lead to signal generator circuitry in a housing such as implanted at block 1402. In an example, block 1406 can include implanting a lead with electrodes that are disposed at or near one or more of the hypoglossal nerve 418, the glossopharyngeal nerve 412, the facial nerve 402, the mandibular branch of the trigeminal nerve 428, the vagus nerve 416, or elsewhere in or near the head or neck of the patient.

At block 1408, the method 1400 can include applying a first neuromodulation therapy to the first cranial nerve target, such as using first electrical signals from the signal generator circuitry (e.g., using the stimulation signal generator circuit 516) and using electrodes of the first electrode lead. In an example, the therapy can include electrical signals that are configured to treat a particular patient disorder, such as can include one or more of OSA, heart failure, hypertension, or one or more other disorders discussed herein, among others.

At block 1410, the method 1400 can include applying a second neuromodulation therapy to the second cranial nerve target, such as using second electrical signals from the signal generator circuitry (e.g., using the stimulation signal generator circuit 516) and using electrodes of the second electrode lead. In an example, applying the first neuromodulation therapy at block 1408 and applying the second neuromodulation therapy at block 1410 can comprise portions of a common therapy that is configured to treat the same disorder or multiple disorders.

Some examples of implantable device housings for cervical implantation are generally represented herein as elongate, prismatic or cylindrical structures. The housings can include enclosures that can be hermetically sealed to protect electronics, circuitry, or other contents from the internal environment of a human body. The housings can be sized and configured to occupy a minimal volume, for example, to enhance patient comfort, or to reduce a risk of infection or complication during implantation, among other reasons.

In an example, a housing can be configured (e.g., sized, shaped, oriented) according to one or more characteristics of an implantation destination. For example, a shape of a housing can optionally be based on characteristics of a triangle in a cervical region of a patient. For example, differently shaped housings can be configured for use in the submental triangle 202 and in the submandibular triangle 206. In an example, a housing for use in a triangle region can include a tapered structure such that, when the housing is implanted, the housing contours generally match or follow corresponding anatomical contours in the cervical region.

Figure 15:
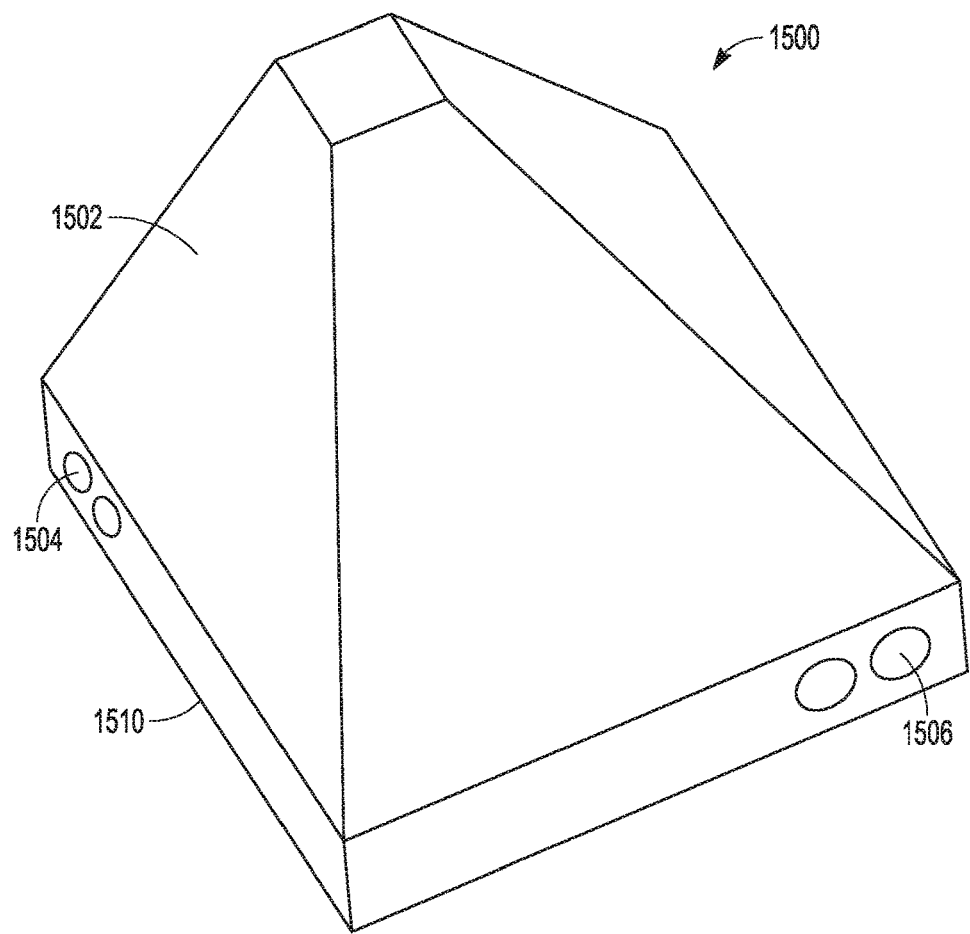
FIG. 15 illustrates generally an example of an implantable device that comprises a tapered housing.

FIG. 15, for example, illustrates generally a tapered housing 1500 for a device to be implanted in or near a triangular cervical region of a patient. The tapered housing 1500 can include a tapered structure, such as a rectangular frustum. The illustrated example of the tapered housing 1500 includes a base surface 1510 and an opposite top surface 1508. The tapered housing 1500 can include tapered sidewalls 1502, such as can include trapezoidal portions, that can extend between the base surface 1510 and the top surface 1508. In an example, a surface area of the top surface 1508 can be less than a surface area of the base surface 1510. One or more headers can be coupled to or integrated with the tapered housing 1500, including at or along any one or more of the side surfaces, base surface 1510, and the top surface 1508.

In an example, the tapered housing 1500 can be configured for implantation inside of at least a portion of the anterior triangle 104 of a patient. In an example, the base surface 1510 can be configured for implantation at or adjacent to a portion of the mylohyoid muscle 114, such that a tapered portion of the housing structure extends away from the mylohyoid muscle 114.

In an example, the tapered housing 1500 can include elongated tapered sidewalls 1502, and a surface characteristic of at least one of the sidewalls can be sized or configured to correspond to, or fit partially or entirely within, contours of a triangle region of the neck, such as within the submandibular triangle 206, the submental triangle 202, or the carotid triangle 302. For example, the first implantable device 608 from the example of FIG. 6 can include a tapered housing with a base portion provided adjacent to the posterior digastric muscle 208, and sidewalls that extend toward a region where the mandible 116 and anterior digastric muscle 204 are proximal or substantially adjacent, such that the device can occupy the submandibular triangle 206. In other words, the device can include a base portion that is sized and configured to correspond to or match a length or width characteristic of the posterior digastric muscle 208 (e.g., between the mandible 116 and the hyoid bone 110). The device can include a sidewall that is configured to correspond to or match a length or width characteristic of the anterior digastric muscle 204 (e.g., between the hyoid bone 110 and the mandible 116), or the device can include a sidewall that is configured to correspond to or match a length or width characteristic of a lower edge portion of the mandible 116 (e.g., between the posterior digastric muscle 208 and the anterior digastric muscle 204).

In an example, the third implantable device 902 from the example of FIG. 9 can include a tapered housing with a base portion provided, for example, adjacent to the omohyoid muscle 306, and sidewalls that extend toward a region where the SCM 106 and the posterior digastric muscle 208 are proximal or substantially adjacent. In other words, the device can include a base portion that is sized and configured to correspond to or match a length or width characteristic of the portion of the omohyoid muscle 306 (e.g., a portion of the omohyoid muscle 306 that is inside the carotid triangle 302). The device can include a sidewall that is configured to correspond to or match a length or width characteristic of the SCM 106 (e.g., a portion of the SCM 106 that is inside the carotid triangle 302), or the device can include a sidewall that is configured to correspond to or match a length or width characteristic of the posterior digastric muscle 208 (e.g., a portion of the posterior digastric muscle 208 bounding the carotid triangle 302, such as between the hyoid bone 110 and the SCM 106). Accordingly, the third implantable device 902 can be configured with a housing that occupies the carotid triangle 302.

In other examples, the tapered housing 1500 can be configured for implantation at or adjacent to various other muscles, tendons, bones, or tissues, such as at or adjacent to a portion of the digastric muscle 112, the SCM 106, the omohyoid muscle 306, or other tissue. Such devices or housings can be configured to occupy all or substantially all of a space available in a triangle region in a neck, such as the submandibular triangle 206, the submental triangle 202, or the carotid triangle 302, among others.

The example of FIG. 15 illustrates the tapered housing 1500 as including various abrupt edges or vertices. One or more of the edges or vertices, or adjacent surfaces, can optionally be chamfered or rounded. In an example, the tapered housing 1500 can include a base or top surface that is at least partially rounded, such that the housing structure is at least partially (or entirely) a conical frustum. In an example, the top surface 1508 or the base surface 1510 can be non-planar, and the top surface 1508 and the base surface 1510 can be at least partially non-parallel.

In an example, the tapered housing 1500 can include various headers on one or more of the surfaces or faces of the housing. In the example of FIG. 15, the tapered housing 1500 includes a first header 1504 and a second header 1506. The headers can be configured to couple circuitry, sensors, or other components inside of the tapered housing 1500 with leads or other devices outside of the tapered housing 1500. In the example of FIG. 15, the first header 1504 and the second header 1506 are provided on adjacent side surfaces of the housing; other positions for the headers can similarly be used. In an example, a position of one or more of the headers can be influenced or determined by an implantation location or a nerve target location.

Figure 16:
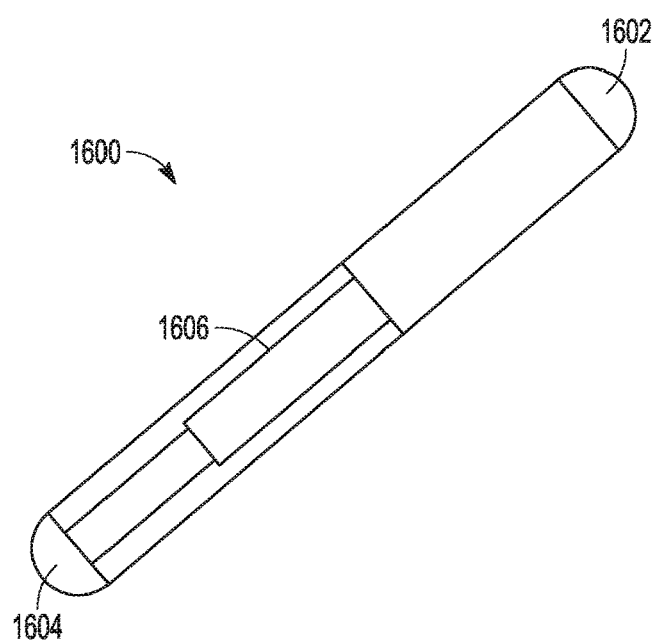
FIG. 16 illustrates generally an example of an implantable device that comprises a capsule housing.

FIG. 16 illustrates generally an example of a cylindrical housing 1600 for a device to be implanted in or near a triangular cervical region of a patient. The cylindrical housing 1600 can include a capsule-shaped structure, such as including a cylinder that extends along a longitudinal axis and includes rounded ends or caps. The cylindrical housing 1600 can enclose signal generator circuitry 1606 and can have multiple headers, such as a first header 1602 and a second header 1604, for interfacing the signal generator circuitry 1606 with various leads. The first header 1602 and the second header 1604 can be disposed at opposite ends of the device or multiple headers can be provided on one end.

In an example, the cylindrical housing 1600 can be configured for implantation along a portion of an anatomic target. For example, the cylindrical housing 1600 can be configured to be coupled to a tissue target in a triangular region. For example, the cylindrical housing 1600 can be configured to be coupled to the anterior digastric muscle 204, or to the posterior digastric muscle 208, or to the SCM 106. In an example, the cylindrical housing 1600 can be configured to be coupled to the SCM 106 inside of the carotid triangle 302, and the cylindrical housing 1600 can be coupled to a lead that extends outside of the carotid triangle 302, such as similarly described above in the example of FIG. 9.

Figure 17:
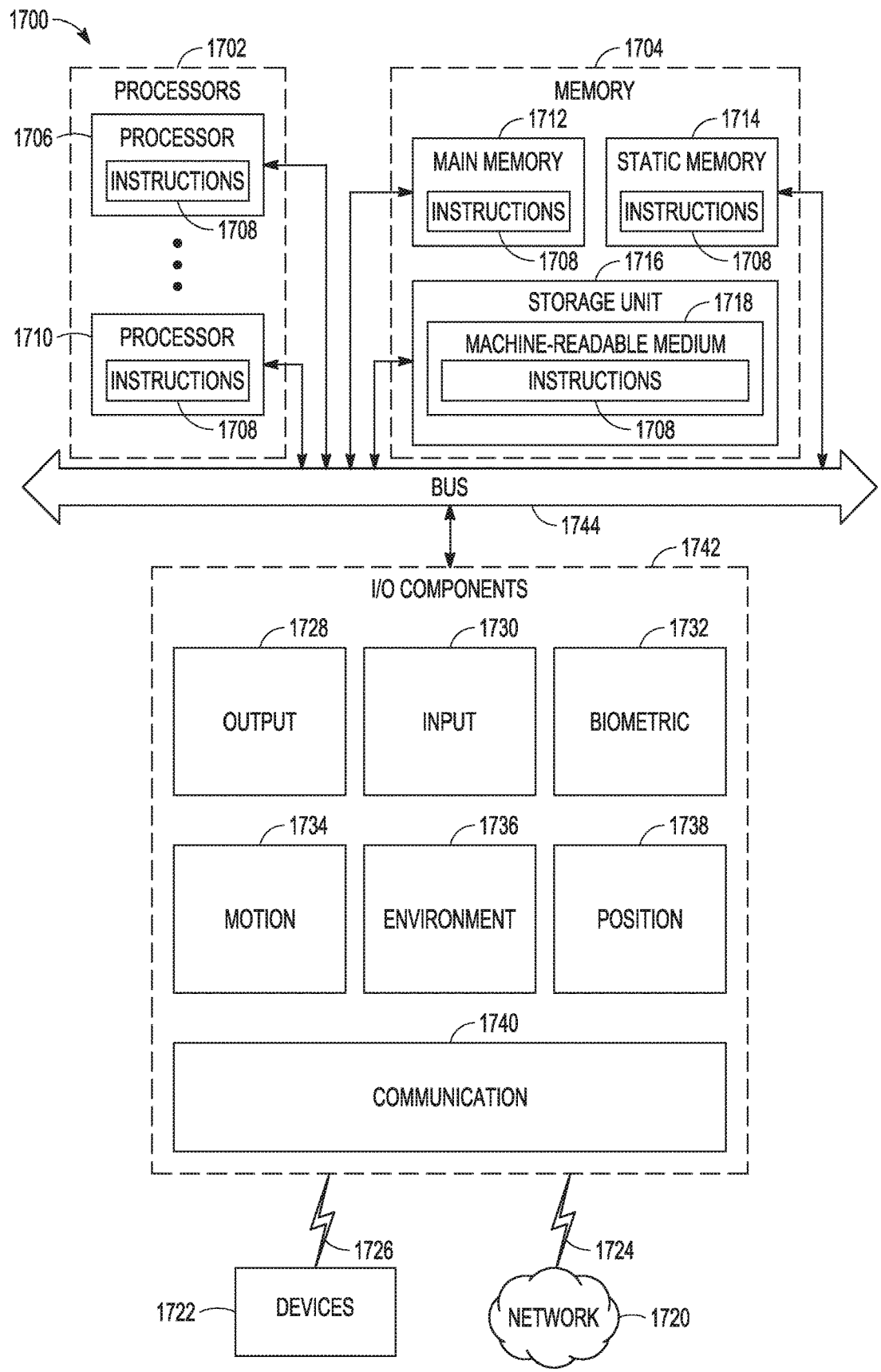
FIG. 17 illustrates generally an example of a machine in the form of a computer system within which a set of instructions may be executed for causing the machine to perform any one or more of the methodologies discussed herein, according to an example embodiment.

FIG. 17 is a diagrammatic representation of a machine 1700 within which instructions 1708 (e.g., software, a program, an application, an applet, an app, or other executable code) for causing the machine 1700 to perform any one or more of the methodologies discussed herein may be executed. The machine 1700 can optionally comprise the implantable system 502, the external system 520, or components or portions thereof, or components or devices that can be coupled to at least one of the implantable system 502 and the external system 520.

In an example, the instructions 1708 may cause the machine 1700 to execute any one or more of the methods, controls, therapy algorithms, signal generation routines, or other processes described herein. The instructions 1708 transform the general, non-programmed machine 1700 into a particular machine 1700 programmed to carry out the described and illustrated functions in the manner described. The machine 1700 may operate as a standalone device or may be coupled (e.g., networked) to other machines. In a networked deployment, the machine 1700 may operate in the capacity of a server machine or a client machine in a server-client network environment, or as a peer machine in a peer-to-peer (or distributed) network environment. The machine 1700 can comprise, but is not limited to, various systems or devices that can communicate with the implantable system 502 or the external system 520, such as can include a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1708, sequentially or otherwise, that specify actions to be taken by the machine 1700. Further, while only a single machine 1700 is illustrated, the term "machine" shall also be taken to include a collection of machines that individually or jointly execute the instructions 1708 to perform any one or more of the methodologies discussed herein.

The machine 1700 may include processors 1702, memory 1704, and I/O components 1742, which may be configured to communicate with each other via a bus 1744. In an example embodiment, the processors 1702 (e.g., a Central Processing Unit (CPU), a Reduced instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 1706 and a processor 1710 that execute the instructions 1708. The term "processor" is intended to optionally include multi-core processors that may comprise two or more independent processors (sometimes referred to as "cores") that may execute instructions contemporaneously. Although FIG. 17 shows multiple processors 1702, the machine 1700 may include a single processor with a single core, a single processor with multiple cores (e.g., a multi-core processor), multiple processors with a single core, multiple processors with multiples cores, or any combination thereof.

The memory 1704 includes a main memory 1712, a static memory 1714, and a storage unit 1716, both accessible to the processors 1702 via the bus 1744. The main memory 1704, the static memory 1714, and storage unit 1716 store the instructions 1708 embodying any one or more of the methodologies or functions described herein. The instructions 1708 may also reside, completely or partially, within the main memory 1712, within the static memory 1714, within a machine-readable medium 1718 within the storage unit 1716, within at least one of the processors 1702 (e.g., within the processor's cache memory), or any suitable combination thereof, during execution thereof by the machine 1700.

The I/O components 1742 may include a variety of components to receive input, provide output, produce output, transmit information, exchange information, capture measurements, and so on. The specific I/O components 1742 that are included in a particular machine will depend on the type of machine. For example, portable machines such as device programmers or mobile phones may include a touch input device or other such input mechanisms, while a headless server machine will likely not include such a touch input device. It will be appreciated that the I/O components 1742 may include other components that are not shown in FIG. 17. In various example embodiments, the I/O components 1742 may include output components 1728 and input components 1730. The output components 1728 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1730 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), physiologic sensor components, and the like.

In further example embodiments, the I/O components 1742 may include biometric components 1732, motion components 1734, environmental components 1736, or position components 1738, among others. For example, the biometric components 1732 can include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1734 can include an acceleration sensor (e.g., an accelerometer), gravitation sensor components, rotation sensor components (e.g., a gyroscope), or similar. The environmental components 1736 can include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1738 can include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1742 further include communication components 1740 operable to couple the machine 1700 to a network 1720 or other devices 1722 via a coupling 1724 and a coupling 1726, respectively. For example, the communication components 1740 may include a network interface component or another suitable device to interface with the network 1720. In further examples, the communication components 1740 may include wired communication components, wireless communication components, cellular communication components, Near Field Communication (NFC) components, Bluetooth components, or Wi-Fi components, among others. The devices 1722 may be another machine or any of a wide variety of peripheral devices such as can include other implantable or external devices.

The various memories (e.g., memory 1704, main memory 1712, static memory 1714, and/or memory of the processors 1702) and/or storage unit 1716 can store one or more sets of instructions and data structures (e.g., software) embodying or used by any one or more of the methodologies or functions described herein. These instructions (e.g., the instructions 1708), when executed by processors 1702, cause various operations to implement the disclosed embodiments, including various neuromodulation or neurostimulation therapies or functions supportive thereof.

The following Aspects provide a non-limiting overview of the neuromodulation systems, methods, and devices discussed herein.

Aspect 1 can include, or can optionally be combined with the subject matter of one or any combination of the following Aspects, to include or use subject matter (such as an apparatus, a method, a means for performing acts, or a machine readable medium including instructions that, when performed by the machine, that can cause the machine to perform acts), such as can include or use an implantable system for neuromodulation of cranial nerves, the system comprising a first housing configured for implantation in an anterior cervical region of a patient, at or under a mandible of the patient, a first electrode lead coupled to the first housing, the first electrode lead comprising at least one electrode configured to be disposed at or near a first cranial nerve target in the patient, and a signal generator circuit provided in the first housing and configured to generate electrical neuromodulation signals for delivery to the cranial nerve target using the at least one electrode of the first electrode lead. The neuromodulation signals can be configured to treat a breathing disorder or a sleep disorder of the patient, among other disorders, such as can be treated using a neuromodulation therapy applied to a cranial nerve or other nerve.

Aspect 2 can include or use, or can optionally be combined with the subject matter of Aspect 1, to optionally include the neuromodulation signals generated by the signal generator circuit configured to treat obstructive sleep apnea.

Aspect 3 can include or use, or can optionally be combined with the subject matter of Aspect 2, to optionally include the first cranial nerve target comprising a main body of a hypoglossal nerve of the patient or a branch of the hypoglossal nerve of the patient.

Aspect 4 can include or use, or can optionally be combined with the subject matter of Aspect 3, to optionally include or use a second electrode lead coupled to the first housing, the second electrode lead comprising at least one electrode configured to be disposed at or near a second cranial nerve target in the patient, and the signal generator circuit can be configured to generate respective neuromodulation signals for delivery to the first and second cranial nerve targets using electrodes on the first and second electrode leads to treat obstructive sleep apnea or one or more other diseases or disorders.

Aspect 5 can include or use, or can optionally be combined with the subject matter of Aspect 4, to optionally include the second cranial nerve target comprising a branch of a trigeminal nerve of the patient.

Aspect 6 can include or use, or can optionally be combined with the subject matter of one or any combination of Aspects 4 or 5, to optionally include the second cranial nerve target comprising a branch of a facial nerve of the patient.

Aspect 7 can include or use, or can optionally be combined with the subject matter of one or any combination of Aspects 4 through 6 to optionally include the second cranial nerve target comprising a ganglion or a branch of a glossopharyngeal nerve of the patient.

Aspect 8 can include or use, or can optionally be combined with the subject matter of one or any combination of Aspects 4 through 7 to optionally include the signal generator circuit configured to provide the neuromodulation signals concurrently to the electrodes of the first and second electrode leads.

Aspect 9 can include or use, or can optionally be combined with the subject matter of Aspect 8, to optionally include or use an electrostimulation vector such as can be produced in response to a first one of the neuromodulation signals. The vector can be configured to modify a different electrostimulation vector such as can be produced in response to a second one of the neuromodulation signals.

Aspect 10 can include or use, or can optionally be combined with the subject matter of one or any combination of Aspects 4 through 9 to optionally include or use the signal generator circuit configured to provide the neuromodulation signals to respective electrodes of the first and second electrode leads in a time-multiplexed manner.

Aspect 11 can include or use, or can optionally be combined with the subject matter of Aspect 10, to optionally include or use the signal generator circuit configured to provide the neuromodulation signals as electrical signal pulses that are at least partially overlapping in time.

Aspect 12 can include or use, or can optionally be combined with the subject matter of one or any combination of Aspects 1 through 11 to optionally include the first cranial nerve target comprising a neural pathway that influences activity of one or more of tongue muscles, mylohyoid muscles, stylohyoid muscles, digastric muscles, or stylopharyngeus muscles of the patient. In the example of Aspect 12, the electrical neuromodulation signals can be configured to treat obstructive sleep apnea or another disorder for the patient.

Aspect 13 can include or use, or can optionally be combined with the subject matter of one or any combination of Aspects 1 through 12 to optionally include the first cranial nerve target in the patient comprising an anterior or posterior branch of a hypoglossal nerve of the patient. In Aspect 13, the first electrode can be configured to be implanted at or near the anterior or posterior branch of the hypoglossal nerve of the patient.

Aspect 14 can include or use, or can optionally be combined with the subject matter of one or any combination of Aspects 1 through 13 to optionally include or use first and second electrodes disposed at different locations along a length of the first electrode lead. In the example of Aspect 14, the first cranial nerve target in the patient can include anterior and/or posterior branches of a hypoglossal nerve of the patient, and the first and second electrodes can be configured to provide neuromodulation signals to the anterior and/or posterior branches of the hypoglossal nerve.

Aspect 15 can include or use, or can optionally be combined with the subject matter of one or any combination of Aspects 1 through 14 to optionally include or use a second electrode lead coupled to the first housing, and the second electrode lead can include at least one electrode configured to be disposed at or near a second cranial nerve target in the patient. In Aspect 15, the first and second cranial nerve targets can be on opposite sides of a sagittal midline of the patient.

Aspect 16 can include or use, or can optionally be combined with the subject matter of Aspect 15, to optionally include or use the first housing comprising first and different second hermetic enclosures that are electrically coupled.

Aspect 17 can include or use, or can optionally be combined with the subject matter of Aspect 16, to optionally include or use the first and second electrode leads coupled to the first and different second hermetic enclosures, respectively.

Aspect 18 can include or use, or can optionally be combined with the subject matter of one or any combination of Aspects 16 or 17 to optionally include or use the first hermetic enclosure comprising a power storage device, and the second hermetic enclosure comprising the signal generator, and the first and second electrode leads coupled to the second hermetic enclosure.

Aspect 19 can include or use, or can optionally be combined with the subject matter of one or any combination of Aspects 16 through 18 to optionally include or use the first and different second hermetic enclosures implanted on opposite sides of a sagittal midline of the patient.

Aspect 20 can include or use, or can optionally be combined with the subject matter of one or any combination of Aspects 16 through 19 to optionally include or use the first and second hermetic enclosures configured to be implanted in respective different anterior triangle regions.

Aspect 21 can include or use, or can optionally be combined with the subject matter of Aspect 20, to optionally include the first hermetic enclosure implanted in a submandibular triangle region of the patient, and the second hermetic enclosure implanted in a muscular triangle region of the patient. In the example of Aspect 21, the submandibular triangle region can be bounded by a body of a mandible and by anterior and posterior portions of a digastric muscle of the patient, and the muscular triangle region of the patient can be bounded by a hyoid bone, a sagittal midline, an omohyoid muscle, and an inferior portion of an sternocleidomastoid muscle of the patient.

Aspect 22 can include or use, or can optionally be combined with the subject matter of one or any combination of Aspects 20 or 21 to optionally include or use the first hermetic enclosure configured to be implanted in a carotid triangle region and the second hermetic enclosure can be configured to be implanted in one of a submandibular triangle region and a submental triangle region of the patient.

Aspect 23 can include or use, or can optionally be combined with the subject matter of one or any combination of Aspects 1 through 22 to optionally include or use a wireless communication coil coupled to a power management circuit in the first housing, and the wireless communication coil can be configured to be disposed in the anterior cervical region of the patient or outside of the anterior cervical region of the patient.

Aspect 24 can include or use, or can optionally be combined with the subject matter of one or any combination of Aspects 1 through 22 to optionally include or use a wireless communication coil coupled to a power management circuit in the first housing, and the wireless communication coil can be configured to be disposed on a mandible of the patient.

Aspect 25 can include or use, or can optionally be combined with the subject matter of one or any combination of Aspects 1 through 22 to optionally include or use the first housing and a wireless communication coil, such as with the coil coupled to circuitry inside the first housing, and configured to be implanted in respective different anterior triangle regions of the patient.

Aspect 26 can include or use, or can optionally be combined with the subject matter of Aspect 25, to optionally include or use a support member for the wireless communication coil, and the support member can be configured to be coupled to anterior and posterior portions of a digastric muscle of the patient.

Aspect 27 can include or use, or can optionally be combined with the subject matter of one or any combination of Aspects 25 or 26 to optionally include or use a support member for the wireless communication coil, and the support member can be configured to be coupled to a mylohyoid muscle of the patient.

Aspect 28 can include, or can optionally be combined with the subject matter of one or any combination of the other Aspects herein to include or use subject matter (such as an apparatus, a method, a means for performing acts, or a machine readable medium including instructions that, when performed by the machine, that can cause the machine to perform acts), such as can include or use an implantable neuromodulation system comprising an elongate first housing configured for implantation in an anterior cervical region of a patient, and a first electrode lead coupled to the first housing and configured to be disposed in a submandibular region. In Aspect 28, at least one electrode on the first electrode lead can be configured to be disposed at or near a first branch of a hypoglossal nerve of the patient, and electrostimulation generation and control circuitry disposed in the first housing can be configured to provide electrostimulation signals to the patient using the first electrode lead. The electrostimulation signals can be configured to treat a sleep disorder or breathing disorder of the patient, among other disorders.

Aspect 29 can include or use, or can optionally be combined with the subject matter of Aspect 28, to optionally include or use the first housing configured for implantation in a submental triangle of the anterior cervical region of the patient.

Aspect 30 can include or use, or can optionally be combined with the subject matter of Aspect 29, to optionally include or use a second electrode lead coupled to the first housing and configured to be disposed in the submandibular region. In Aspect 30, at least one electrode on the second electrode lead can be configured to be disposed at or near a second branch of the hypoglossal nerve of the patient.

Aspect 31 can include or use, or can optionally be combined with the subject matter of Aspect 30, to optionally include or use electrodes on the first and second electrode leads configured to be disposed at or near different positions of anterior and/or posterior branches of the hypoglossal nerve.

Aspect 32 can include or use, or can optionally be combined with the subject matter of one or any combination of Aspects 30 or 31 to optionally include or use electrodes on the first and second electrode leads configured to be disposed on respective different sides of a sagittal midline of the patient, and the electrostimulation generation and control circuitry can be configured to provide a bilateral electrostimulation therapy to the branches of the hypoglossal nerves.

Aspect 33 can include or use, or can optionally be combined with the subject matter of one or any combination of Aspects 28 through 32 to optionally include or use the first housing comprising a cylindrical housing structure having a longitudinal axis, and the first housing can be configured for implantation at or adjacent to a mandible of the patient.

Aspect 34 can include or use, or can optionally be combined with the subject matter of one or any combination of Aspects 28 through 33 to optionally include or use the first housing comprising a rectangular frustum structure with a base surface configured to be oriented posteriorly in the submandibular region, and a top surface configured to be oriented anteriorly in the submandibular region, and an area of the base surface can exceed an area of the top surface.

Aspect 35 can include or use, or can optionally be combined with the subject matter of one or any combination of Aspects 28 through 33 to optionally include or use the first housing comprising sidewalls that are contoured to correspond to contours of an anatomic triangle in the submandibular region.

Aspect 36 can include or use, or can optionally be combined with the subject matter of one or any combination of Aspects 28 through 35 to optionally include or use an anchor configured to physically and mechanically couple a base portion of the first housing to a mandible.

Aspect 37 can include or use, or can optionally be combined with the subject matter of one or any combination of Aspects 28 through 33 to optionally include or use the first housing comprising a truncated prism structure with a base portion that can be configured to be oriented adjacent to at least one of a digastric muscle surface, a mylohyoid muscle surface, or a mandible of the patient.

Aspect 38 can include or use, or can optionally be combined with the subject matter of Aspect 37, to optionally include or use an anchor configured to couple the first housing to a hyoid bone of the patient.

Aspect 39 can include or use, or can optionally be combined with the subject matter of Aspect 37, to optionally include or use an anchor to couple the first housing to at least one of an omohyoid muscle, a digastric muscle, or a digastric tendon of the patient.

Aspect 40 can include or use, or can optionally be combined with the subject matter of one or any combination of Aspects 28 through 39 to optionally include the first housing configured for implantation such that a longitudinal axis of the housing can be provided substantially parallel to a sternocleidomastoid muscle of the patient.

Aspect 41 can include or use, or can optionally be combined with the subject matter of one or any combination of Aspects 28 through 40 to optionally include or use a second housing configured for implantation in the anterior cervical region of the patient. The second housing can be electrically coupled to at least one of the first housing and the first electrode lead.

Aspect 42 can include or use, or can optionally be combined with the subject matter of Aspect 41, to optionally include the first and second housings configured for implantation on respective different sides of a sagittal midline of the patient.

Aspect 43 can include, or can optionally be combined with the subject matter of one or any combination of the other Aspects herein to include or use subject matter (such as an apparatus, a method, a means for performing acts, or a machine readable medium including instructions that, when performed by the machine, that can cause the machine to perform acts), such as can include or use a method for treating a sleep disorder or a breathing disorder of a patient, the method comprising providing an implantable neuromodulation device in an anterior cervical region of a patient, providing a first electrode lead, coupled to signal generator circuitry in the device, at or near a first cranial nerve target in the patient, and applying a first neuromodulation signal to the first cranial nerve target using first electrical signals from the signal generator circuitry and using electrodes of the first electrode lead. In Aspect 43, the first electrical signals can be configured to treat the sleep disorder or breathing disorder of the patient.

Aspect 44 can include or use, or can optionally be combined with the subject matter of Aspect 43, to optionally include applying the first neuromodulation signal to a hypoglossal nerve of the patient to treat obstructive sleep apnea.

Aspect 45 can include or use, or can optionally be combined with the subject matter of one or any combination of Aspects 43 or 44 to optionally include applying a neuromodulation therapy to one or more of a hypoglossal nerve, a trigeminal nerve, a vagus nerve, a glossopharyngeal nerve, and a facial nerve of the patient.

Aspect 46 can include or use, or can optionally be combined with the subject matter of one or any combination of Aspects 43 through 45 to optionally include coupling the housing and the electrode lead to tissue in the anterior cervical region of the patient.

Aspect 47 can include or use, or can optionally be combined with the subject matter of Aspect 46, to optionally include coupling the housing to a digastric muscle or to a digastric tendon inside the patient body.

Aspect 48 can include or use, or can optionally be combined with the subject matter of one or any combination of Aspects 46 or 47 to optionally include coupling the housing to a mylohyoid muscle of the patient.

Aspect 49 can include or use, or can optionally be combined with the subject matter of one or any combination of Aspects 43 through 48 to optionally include providing a second electrode lead, coupled to the signal generator circuitry in the device housing, at or near a second cranial nerve target in the patient, and applying a second neuromodulation signal to the second cranial nerve target using second electrical signals from the signal generator circuitry and using electrodes of the second electrode lead. In Aspect 49, the second electrical signals can be configured to treat one or more of heart failure, hypertension, and atrial fibrillation.

Aspect 50 can include or use, or can optionally be combined with the subject matter of Aspect 49, to optionally include applying the first neuromodulation signal to a hypoglossal nerve, and applying the second neuromodulation signal to at least one of a vagus nerve, a facial nerve, and a glossopharyngeal nerve.

Aspect 51 can include or use, or can optionally be combined with the subject matter of one or any combination of Aspects 49 or 50 to optionally include applying the first and second neuromodulation signals concurrently to the first and second cranial nerve targets.

Aspect 52 can include or use, or can optionally be combined with the subject matter of one or any combination of Aspects 49 through 51 to optionally include applying the neuromodulation signals in a time-multiplexed manner to the first and second cranial nerve targets.

Aspect 53 can include or use, or can optionally be combined with the subject matter of one or any combination of Aspects 49 through 52 to optionally include applying respective pulse signals to the targets, and the pulses can be at least partially overlapping in time.

Aspect 54 can include, or can optionally be combined with the subject matter of one or any combination of the other Aspects herein to include or use subject matter (such as an apparatus, a method, a means for performing acts, or a machine readable medium including instructions that, when performed by the machine, that can cause the machine to perform acts), such as can include or use an implantable neuromodulation system comprising a first housing disposed in a first cervical triangle region of a patient, a second housing disposed in a different second cervical triangle region of the patient, and an interface coupling first circuitry in the first housing and second circuitry in the second housing. In Aspect 54, the first circuitry can include signal generator circuitry configured to generate neuromodulation signals to treat a breathing disorder or a sleep disorder of the patient, among other disorders, and the second circuitry can include a power storage device.

Aspect 55 can include or use, or can optionally be combined with the subject matter of Aspect 54, to optionally include the first and second cervical triangle regions being separated by a portion of a digastric muscle of the patient.

Aspect 56 can include or use, or can optionally be combined with the subject matter of one or any combination of Aspects 54 or 55 to optionally include or use circuitry configured to wirelessly receive a power signal from a source external to a body of the patient.

Aspect 57 can include or use, or can optionally be combined with the subject matter of one or any combination of Aspects 54 through 56 to optionally include the first housing configured to be implanted in one of a submandibular triangle and a submental triangle of the patient, and the second housing configured to be implanted in the other one of the submandibular triangle and the submental triangle of the patient, and the first and second housings can be differently sized and shaped.

Aspect 58 can include or use, or can optionally be combined with the subject matter of one or any combination of Aspects 54 through 57 to optionally include the second housing being volumetrically larger than the first housing.

Aspect 59 can include or use, or can optionally be combined with the subject matter of one or any combination of Aspects 54 through 58 to optionally include or use one or more physiologic status sensors disposed in or coupled to one of the first and second housings. In Aspect 59, the one or more physiologic status sensors can be configured to measure information about a respiration, heart rate, blood pressure, sympathetic tone, parasympathetic tone, posture, activity level, body impedance, or electric activity of the patient. In Aspect 59, the signal generator circuitry can be configured to generate the neuromodulation signals to treat obstructive sleep apnea or other disorder based on the information from the physiologic status sensor.

Each of these non-limiting Aspects can stand on its own, or can be combined in various permutations or combinations with one or more of the other Aspects and examples discussed herein.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part, such as using the implantable system 502, the external system 520, the machine 1700, or using the other systems, devices, or components discussed herein. Some examples can include a computer-readable medium or machine-readable medium encoded with instructions operable to configure an electronic device to perform methods, such as neuromodulation therapy control methods, as described in the above examples, such as to treat one or more diseases or disorders. In an example, the instructions can include instructions to receive sensor data from one or more physiologic sensors and, based on the sensor data, titrate a therapy. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for treating a sleep disorder or a breathing disorder of a patient, the method comprising:
    providing an implantable neuromodulation device housing in an anterior cervical region of a patient between a mylohyoid muscle of the patient and a digastric muscle of the patient;
    coupling the implantable neuromodulation device housing to first tissue in the anterior cervical region of the patient;
    providing a first electrode lead, coupled to a portion of the device housing and to signal generator circuitry inside the device housing, at or near a first cranial nerve target in the patient, wherein the signal generator circuitry is coupled to power storage circuitry that is inside the device housing;
    coupling the first electrode lead to second tissue in the anterior cervical region of the patient; and
    applying a first neuromodulation signal to the first cranial nerve target using first electrical signals from the signal generator circuitry and using electrodes of the first electrode lead, wherein the first electrical signals are configured to treat the sleep disorder or breathing disorder of the patient.

2. The method of claim 1, wherein the applying the first neuromodulation signal to the first cranial nerve target includes applying the first neuromodulation signal to a hypoglossal nerve of the patient to treat obstructive sleep apnea.

3. The method of claim 1, wherein the first cranial nerve target comprises one or more of a hypoglossal nerve, a trigeminal nerve, a vagus nerve, a glossopharyngeal nerve, and a facial nerve of the patient.

4. The method of claim 1, wherein coupling the device housing to the first tissue comprises coupling the device housing to a digastric muscle or to a digastric tendon.

5. The method of claim 1, wherein coupling the device housing to the first tissue comprises coupling the device housing to a mylohyoid muscle of the patient.

6. The method of claim 1, further comprising:
providing a second electrode lead, coupled to the signal generator circuitry in the device housing, at or near a second cranial nerve target in the patient; and
applying a second neuromodulation signal to the second cranial nerve target using second electrical signals from the signal generator circuitry and using electrodes of the second electrode lead.

7. The method of claim 6, wherein the first cranial nerve target comprises a hypoglossal nerve, and wherein the second cranial nerve target comprises one or more of a vagus nerve, a facial nerve, and a glossopharyngeal nerve.

8. The method of claim 6, wherein applying the first and second neuromodulation signals includes applying the signals concurrently to the first and second cranial nerve targets.

9. The method of claim 6, wherein applying the first and second neuromodulation signals includes applying the signals in a time-multiplexed manner to the first and second cranial nerve targets.

10. The method of claim 6, wherein applying the first and second neuromodulation signals includes applying respective pulse signals to the targets, wherein the pulses are at least partially overlapping in time.

11. The method of claim 6, wherein the second electrical signals are configured to treat one or more of heart failure, hypertension, and atrial fibrillation.

12. The method of claim 6, wherein applying the first and second cranial nerve targets are on opposite sides of a sagittal midline of the patient.

13. The method of claim 1, wherein providing the implantable neuromodulation device housing in the region includes providing the implantable neuromodulation device housing inferior to the mylohyoid muscle of the patient and superior to at least a portion of the digastric muscle of the patient.

14. The method of claim 13, wherein the implantable neuromodulation device housing includes a first portion configured to be disposed adjacent to the mylohyoid muscle of the patient and the housing includes a second portion that extends toward a superior surface of the digastric muscle of the patient.

15. A method for treating a sleep disorder or a breathing disorder of a patient, the method comprising:
providing an implantable neuromodulation device housing between a mylohyoid muscle and a digastric muscle in a submental triangular region of the patient;
coupling the implantable neuromodulation device housing to first tissue in the submental triangular region of the patient, wherein the device housing encloses a signal generator circuit and a power storage circuit;
electrically coupling an electrode of a first electrode lead to the signal generator circuit inside the device housing;
coupling the electrode to a first cranial nerve target in or adjacent to the submental triangular region of the patient; and
applying a first neuromodulation signal to the first cranial nerve target using first electrical signals from the signal generator circuit and the electrode of the first electrode lead, wherein the first neuromodulation signal is configured to treat the sleep disorder or breathing disorder of the patient.

16. The method of claim 15, wherein coupling the electrode to the first cranial nerve target includes coupling a cuff electrode to a hypoglossal nerve of the patient to treat obstructive sleep apnea.

17. The method of claim 15, wherein coupling the electrode to the first cranial nerve target includes coupling a cuff electrode to one or more of a hypoglossal nerve, a trigeminal nerve, a vagus nerve, a glossopharyngeal nerve, and a facial nerve of the patient.

18. The method of claim 15, wherein coupling the neuromodulation device housing to the first tissue in the submental triangular region of the patient includes coupling the neuromodulation device housing to a digastric muscle.

19. The method of claim 15, wherein coupling the neuromodulation device housing to the first tissue in the submental triangular region of the patient includes coupling the neuromodulation device housing to a digastric tendon.

20. The method of claim 15, wherein coupling the neuromodulation device housing to the first tissue in the submental triangular region of the patient includes coupling the neuromodulation device housing to a mylohyoid muscle of the patient.

21. The method of claim 15, comprising:
electrically coupling a second electrode of a second electrode lead to the signal generator circuit inside the device housing;
coupling the second electrode to a second cranial nerve target in the patient; and
applying a second neuromodulation signal to the second cranial nerve target using second electrical signals from the signal generator circuit and the second electrode of the second electrode lead;
wherein the second electrical signals are configured to treat one or more of heart failure, hypertension, and atrial fibrillation.

22. The method of claim 15, comprising:
electrically coupling a second electrode of a second electrode lead to the signal generator circuit inside the device housing;
coupling the second electrode to a second cranial nerve target in the patient; and
applying a second neuromodulation signal to the second cranial nerve target using second electrical signals from the signal generator circuit and the second electrode of the second electrode lead;
wherein the first cranial nerve target comprises a hypoglossal nerve, and wherein the second cranial nerve target comprises one or more of a vagus nerve, a facial nerve, and a glossopharyngeal nerve.

* * * * *